United States Patent
Broome et al.

(10) Patent No.: US 10,428,331 B2
(45) Date of Patent: Oct. 1, 2019

(54) TARGETED NANOCARRIERS FOR THE ADMINISTRATION OF IMMUNOSUPPRESSIVE AGENTS

(71) Applicant: MUSC FOUNDATION FOR RESEARCH DEVELOPMENT, Charleston, SC (US)

(72) Inventors: Ann-Marie Broome, Mt. Pleasant, SC (US); Suraj Dixit, Charleston, SC (US); Satish Nadig, Johns Island, SC (US); Carl Atkinson, Mt. Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 304 days.

(21) Appl. No.: 15/107,536

(22) PCT Filed: Jan. 14, 2015

(86) PCT No.: PCT/US2015/011310
§ 371 (c)(1),
(2) Date: Jun. 23, 2016

(87) PCT Pub. No.: WO2015/108912
PCT Pub. Date: Jul. 23, 2015

(65) Prior Publication Data
US 2016/0317670 A1   Nov. 3, 2016

Related U.S. Application Data

(60) Provisional application No. 61/928,277, filed on Jan. 16, 2014, provisional application No. 61/974,872, filed on Apr. 3, 2014.

(51) Int. Cl.

| A61K 39/395 | (2006.01) |
|---|---|
| C12N 15/117 | (2010.01) |
| A61K 31/365 | (2006.01) |
| A61K 31/436 | (2006.01) |
| A61K 31/713 | (2006.01) |
| A61K 35/17 | (2015.01) |
| A61K 38/13 | (2006.01) |
| A61K 38/17 | (2006.01) |
| A61K 38/20 | (2006.01) |
| C12N 15/11 | (2006.01) |
| A61K 31/395 | (2006.01) |
| A61K 47/62 | (2017.01) |
| A61K 47/69 | (2017.01) |
| A61K 35/12 | (2015.01) |

(52) U.S. Cl.
CPC .......... *C12N 15/117* (2013.01); *A61K 31/365* (2013.01); *A61K 31/395* (2013.01); *A61K 31/436* (2013.01); *A61K 31/713* (2013.01); *A61K 35/17* (2013.01); *A61K 38/13* (2013.01); *A61K 38/1793* (2013.01); *A61K 38/2013* (2013.01); *A61K 47/62* (2017.08); *A61K 47/6909* (2017.08); *C12N 15/111* (2013.01); *A61K 2035/124* (2013.01); *C12N 2310/14* (2013.01); *C12N 2310/17* (2013.01); *C12N 2320/32* (2013.01)

(58) Field of Classification Search
None
See application file for complete search history.

(56) References Cited

U.S. PATENT DOCUMENTS

| 4,789,633 A | 12/1988 | Huang et al. |
|---|---|---|
| 2011/0177155 A1 | 7/2011 | Peer et al. |

FOREIGN PATENT DOCUMENTS

WO   2015066535 A1   5/2015

OTHER PUBLICATIONS

The International Search Report and Written Opinion, dated Apr. 1, 2015, in the related PCT Application No. PCT/US15/11310.
The extended European Search Report, dated Jul. 19, 2017, in the related European Application No. 15737362.2.
Tagalakis A D et al: "Integrin-targeted nanocomplexes for tumour specific delivery and therapy by systemic administration", Biomaterials, Elsevier Science Publishers BV., Barking, GB, vol. 32, No. 5, Feb. 1, 2011(Feb. 1, 2011), pp. 1370-1376.
Satish N. Nadig et al: "Immunosuppressive nano-therapeutic micelles downregulate endothelial cell inflammation and immunogenicity", RSC ADV., vol. 5, No. 54, May 1, 2015(May 1, 2015), pp. 43552-43562.

*Primary Examiner* — Yunsoo Kim

(57) ABSTRACT

Disclosed is a nanocarrier-containing immunosuppressive agent that is targeted to C3 breakdown products, integrin, or a combination thereof, to reduce the deleterious systemic effects of the immunosuppressive agent. Also disclosed is a method for suppressing an allo-immune response in a subject, such as one that can occur after an allograft transplantation.

15 Claims, 13 Drawing Sheets
Specification includes a Sequence Listing.

SEQUENCE LISTING

<160> NUMBER OF SEQ ID NOS: 1

<210> SEQ ID NO 1
<211> LENGTH: 1092
<212> TYPE: PRT
<213> ORGANISM: homo sapiens

<400> SEQUENCE: 1

Met Gly Ala Ala Gly Leu Leu Gly Val Phe Leu Ala Leu Val Ala Pro

-continued

```
1               5                   10                  15
Gly Val Leu Gly Ile Ser Cys Gly Ser Pro Pro Ile Leu Asn Gly
            20                  25                  30

Arg Ile Ser Tyr Tyr Ser Thr Pro Ile Ala Gly Thr Val Ile Arg
            35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
                100                 105                 110

Ser Val Thr Phe Ala Cys Lys Thr Asn Phe Ser Met Asn Gly Asn Lys
                115                 120                 125

Ser Val Trp Cys Gln Ala Asn Asn Met Trp Gly Pro Thr Arg Leu Pro
            130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Gly Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
                260                 265                 270

Glu Ile Phe Cys Pro Ser Pro Pro Ile Leu Asn Gly Arg His Ile
            275                 280                 285

Gly Asn Ser Leu Ala Asn Val Ser Tyr Gly Ser Ile Val Thr Tyr Thr
    290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
                325                 330                 335

Gly Pro Ala Pro Arg Cys Glu Leu Ser Thr Ser Ala Val Gln Cys Pro
                340                 345                 350

His Pro Gln Ile Leu Arg Gly Arg Met Val Ser Gly Gln Lys Asp Arg
            355                 360                 365

Tyr Thr Tyr Asn Asp Thr Val Ile Phe Ala Cys Met Phe Gly Phe Thr
        370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
                405                 410                 415

Leu Asn Gly Gln Lys Glu Asp Arg His Met Val Arg Phe Asp Pro Gly
            420                 425                 430
```

```
Thr Ser Ile Lys Tyr Ser Cys Asn Pro Gly Tyr Val Leu Val Gly Glu
        435                 440                 445

Glu Ser Ile Gln Cys Thr Ser Glu Gly Val Trp Thr Pro Pro Val Pro
450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
                    485                 490                 495

Glu Gly Tyr Lys Leu Ser Gly Ser Val Tyr Gln Glu Cys Gln Gly Thr
                500                 505                 510

Ile Pro Trp Phe Met Glu Ile Arg Leu Cys Lys Glu Ile Thr Cys Pro
            515                 520                 525

Pro Pro Pro Val Ile Tyr Asn Gly Ala His Thr Gly Ser Ser Leu Glu
530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
                565                 570                 575

Thr Ser Asn Asp Gln Glu Arg Gly Thr Trp Ser Gly Pro Ala Pro Leu
                580                 585                 590

Cys Lys Leu Ser Leu Leu Ala Val Gln Cys Ser His Val His Ile Ala
            595                 600                 605

Asn Gly Tyr Lys Ile Ser Gly Lys Glu Ala Pro Tyr Phe Tyr Asn Asp
            610                 615                 620

Thr Val Thr Phe Lys Cys Tyr Ser Gly Phe Thr Leu Lys Gly Ser Ser
625                 630                 635                 640

Gln Ile Arg Cys Lys Ala Asp Asn Thr Trp Asp Pro Glu Ile Pro Val
                645                 650                 655

Cys Glu Lys Gly Cys Gln Ser Pro Pro Gly Leu His His Gly Arg His
                660                 665                 670

Thr Gly Gly Asn Thr Val Phe Phe Val Ser Gly Met Thr Val Asp Tyr
            675                 680                 685

Thr Cys Asp Pro Gly Tyr Leu Leu Val Gly Asn Lys Ser Ile His Cys
            690                 695                 700

Met Pro Ser Gly Asn Trp Ser Pro Ser Ala Pro Arg Cys Glu Glu Thr
705                 710                 715                 720

Cys Gln His Val Arg Gln Ser Leu Gln Glu Leu Pro Ala Gly Ser Arg
                725                 730                 735

Val Glu Leu Val Asn Thr Ser Cys Gln Asp Gly Tyr Gln Leu Thr Gly
                740                 745                 750

His Ala Tyr Gln Met Cys Gln Asp Ala Glu Asn Gly Ile Trp Phe Lys
            755                 760                 765

Lys Ile Pro Leu Cys Lys Val Ile His Cys His Pro Pro Pro Val Ile
            770                 775                 780

Val Asn Gly Lys His Thr Gly Met Met Ala Glu Asn Phe Leu Tyr Gly
785                 790                 795                 800

Asn Glu Val Ser Tyr Glu Cys Asp Gln Gly Phe Tyr Leu Leu Gly Glu
                805                 810                 815

Lys Lys Leu Gln Cys Arg Ser Asp Ser Lys Gly His Gly Ser Trp Ser
                820                 825                 830

Gly Pro Ser Pro Gln Cys Leu Arg Ser Pro Pro Val Thr Arg Cys Pro
                835                 840                 845
```

-continued

```
Asn Pro Glu Val Lys His Gly Tyr Lys Leu Asn Lys Thr His Ser Ala
    850             855             860
Tyr Ser His Asn Asp Ile Val Tyr Val Asp Cys Asn Pro Gly Phe Ile
865             870             875             880
Met Asn Gly Ser Arg Val Ile Arg Cys His Thr Asp Asn Thr Trp Val
            885             890             895
Pro Gly Val Pro Thr Cys Ile Lys Lys Ala Phe Ile Gly Cys Pro Pro
            900             905             910
Pro Pro Lys Thr Pro Asn Gly Asn His Thr Gly Gly Asn Ile Ala Arg
        915             920             925
Phe Ser Pro Gly Met Ser Ile Leu Tyr Ser Cys Asp Gln Gly Tyr Leu
    930             935             940
Leu Val Gly Glu Ala Leu Leu Leu Cys Thr His Glu Gly Thr Trp Ser
945             950             955             960
Gln Pro Ala Pro His Cys Lys Glu Val Asn Cys Ser Ser Pro Ala Asp
                965             970             975
Met Asp Gly Ile Gln Lys Gly Leu Glu Pro Arg Lys Met Tyr Gln Tyr
            980             985             990
Gly Ala Val Val Thr Leu Glu Cys Glu Asp Gly Tyr Met Leu Glu Gly
        995             1000            1005
Ser Pro Gln Ser Gln Cys Gln Ser Asp His Gln Trp Asn Pro Pro
    1010            1015            1020
Leu Ala Val Cys Arg Ser Arg Ser Leu Ala Pro Val Leu Cys Gly
    1025            1030            1035
Ile Ala Ala Gly Leu Ile Leu Leu Thr Phe Leu Ile Val Ile Thr
    1040            1045            1050
Leu Tyr Val Ile Ser Lys His Arg Ala Arg Asn Tyr Tyr Thr Asp
    1055            1060            1065
Thr Ser Gln Lys Glu Ala Phe His Leu Glu Ala Arg Glu Val Tyr
    1070            1075            1080
Ser Val Asp Pro Tyr Asn Pro Ala Ser
    1085            1090
```

TARGETED NANOCARRIERS FOR THE ADMINISTRATION OF IMMUNOSUPPRESSIVE AGENTS

CROSS-REFERENCE TO RELATED APPLICATIONS

This application is a National Stage Application of PCT/US2015/011310 filed Jan. 14, 2015, which claims benefit of U.S. Provisional Application No. 61/928,277, filed Jan. 16, 2014, and U.S. Provisional Application No. 61/974,872, filed Apr. 3, 2014. Each of prior mentioned applications is hereby incorporated by reference herein in its entirety.

BACKGROUND

Organ transplantation has become an accepted modality for the treatment of end-stage organ failure. The field of transplant medicine has made tremendous strides within the last thirty years, allowing for newer, more potent immunosuppressive medications rendering acute rejection episodes less frequent and less aggressive. In spite of these accomplishments, chronic allograft dysfunction (CAD) remains a leading cause of graft loss in the long term. Various translational research efforts have identified pathways and potential therapeutics that may allay the effects of CAD by conferring a tolerogenic phenotype in allograft recipients both in mouse and man.

Cellular therapies including regulatory T cells (Treg) have garnered attention in the literature for their natural and adaptive ability to suppress allo-immune responses and provide long-term graft survival in various mouse and humanized experimental models. Harnessing the ability of various regulatory-type cells to confer a tolerogenic phenotype is under vigorous translational and clinical investigations at present, and is now in the early stages of clinical trials. Additionally, the protective ability of Treg may be bolstered by the use of pharmaco-therapeutics such as rapamycin, which selectively allows for the proliferation of Treg while inhibiting the growth of effector T cells. When combined, sub-therapeutic doses of both therapies have been shown to successfully attenuate transplant arteriosclerosis, a pathognomonic hallmark of chronic rejection, in humanized mouse models. Despite these data, rapamycin continues to be used only sparingly in the peri-operative period due to various deleterious systemic effects of poor wound healing, proteinuria, hyperlipidemia, and poor patient tolerance, to name a few.

SUMMARY

Disclosed are compositions and methods that circumvent the systemic side effects of immunotherapeutics and protect the organ graft by specifically delivering these medications directly to the endothelium of grafted tissues to reduce local injury, inflammation, allopresentation, and the harmful side effects associated with their systemic counterparts. Complement component 3 (C3) breakdown products deposit in allografts early post-transplantation as a response to ischemia-reperfusion injury, an unavoidable event in all solid organ transplants. Moreover, the integrin, αVβ3, is up-regulated following transplantation, and β3 polymorphisms are associated with organ rejection. Therefore, disclosed is a nanocarrier-containing immunosuppressive agent that is targeted to C3 breakdown products, integrin, or a combination thereof, to reduce the deleterious systemic effects of the immunosuppressive agent delivered systemically. The targeted nanocarrier can comprise an effective amount of an immunosuppressive agent (e.g., an mTOR inhibitor such as rapamycin) encapsulated in a micelle, liposome, or polymeric nanoparticle that comprises on its surface one or more agents, such as recombinant proteins, antibodies, or peptides, that binds C3 breakdown products (e.g., iC3b, C3dg and/or C3d), integrins (e.g., αVβ3), or a combination thereof. For example, in some cases, the targeted nanocarrier is targeted to both a C3 breakdown product and an integrin.

In some embodiments, the surface agent comprises Complement Receptor type 2 (CR2) recombinant protein or a peptide variant and/or fragment thereof capable of binding C3 breakdown products. In addition to CR2 targeting, in some embodiments antibodies against C3 split fragments, such as anti-iC3b, anti-C3d, and anti-C3dg, and antibodies/recombinant proteins raised against neo-epitopes exposed by reperfusion injury, such as anti-annexin 4 (B4) and anti-phospholipids (C2) antibodies can be used as surface targeting agents.

In some embodiments, the surface agent comprises a peptide or peptidomimetic that binds integrin. For example, the surface agent can comprise a Arg-Gly-Asp (RGD) peptide or peptidomimetic. In some cases, the surface agent comprises a cyclized arginine-glycineaspartic acid (cRGD).

The surface agent can also be a fusion protein linking the peptide that binds C3 breakdown products or integrins to another moiety. For example, the moiety can be a label (e.g., fluorochrome), a complement inhibitor (Crry, fH, Daf, MCP, CR1, CD59), or a combination thereof.

To optimize vascular permeability and penetration into tissue and cells, the nanocarrier can range from 1-100 nm in mean diameter, including about 5 nm to 100 nm, or about 10 nm to 15 nm. In addition with its multifunctional character (large surface area due to small size, surface can be tailored with different functionalities), the nanocarrier behaves like a stealth agent and can evade immune response from the host system due to surface modifications including pegylation.

In some embodiments, the targeted nanocarrier is a micelle or liposome. The micelle or liposome can be formed from any biocompatible surfactant molecules capable of encapsulating the immunosuppressive agent. For example, the nanocarrier can be composed of amino-polyethylene glycol-phosphatidylethanolamine (PEG-PE-Amine) Other lipid molecules that can be used include: phosphoholines (DSPC), DC cholesterol, HSPC soy, 1,2-dioleoyl-3-trimethylammonium-propane (DOTA). Another alternative is to use chitosan as a drug delivery agent. Chitosan is FDA approved and biocompatible and is known to encapsulate various molecules including drugs and nanoparticles. pH sensitive forms of chitosan are also available.

In some cases, release of the immunosuppressive agent is triggered by the decrease in endosomal pH initiated by cellular uptake. Therefore, the targeted nanocarrier can comprise a micelle, liposome, or polymeric nanoparticle that is pH sensitive.

In some embodiments, the micelle or liposome can use temperature sensitive co-polymers like poly(N-isopropylacrylamide-co-acrylic acid mixed with lipids to create a mixed polymeric micelle or a liposomal system. For example, the transition temperatures of the polymers can be around 40 degrees Celsius.

The immunosuppressive agent can be any suitable immunosuppressive agent. In some embodiments, immunosuppressive agent can be an mTOR inhibitor, such as rapamycin or a rapamycin derivative. Examples of rapamycin derivatives include esters, ethers, carbamates, oximes, hydrazones, and hydroxylamines of rapamycin, as well as compounds in which one or more of the functional groups attached to the attached to the rapamycin nucleus have been modified, for example, through reduction or oxidation. In certain embodiments, the immunosuppressive agent is rapamycin, temsirolimus, everolimus, ridaforolimus, pimecrolimus, merilimus, zotarolimus, TOP216, TAFA93, nab-rapamycin, or tacrolimus. In certain embodiments, the immunosuppressive agent is an anti-CD25 agent, such as dacluzimab or basiliximab. In certain embodiments, the immunosuppressive agent is an NFκB inhibitor, such as A20. In certain embodiments, the immunosuppressive agent is a Jak3 inhibitor, such as tofacitinib or tasocitinib. In certain embodiments, the immunosuppressive agent is a costimulation blockade, such as belatacept or abatacept. In certain embodiments, the immunosuppressive agent is a cell-cycle inhibitor, such as mycophenolate mofetil or mycophenolic acid. In certain embodiments, the immunosuppressive agent is a B-cell proteosome inhibitor, such as bortezomib. In certain embodiments, the immunosuppressive agent is a Complement C siRNA inhibitor. In certain embodiments, the immunosuppressive agent comprises IL-2R alpha or a derivative or analogue thereof.

Also disclosed is a method for suppressing an alloimmune response in a subject, such as one that can occur after an allograft transplantion. The method can comprise administering to the subject before, during, or after an allograft transplantation an effective amount of composition comprising immunosuppressive agent (e.g., an mTOR inhibitor such as rapamycin) encapsulated in a nanocarrier that specifically targets C3 breakdown products. For example, the method can comprise administering any of the targeted nanocarriers disclosed herein. The method can also comprise administering to the subject a composition comprising regulatory T cells (Treg). Other combined therapies include: immature/tolerogenic dendritic cells, donor specific antigen, mesenchymal stem cells, regulatory macrophages, regulatory CD8+ cells, regulatory B cells, and myeloid derived suppressor cells.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A shows size calculation using DLS of RaM and TRaM demonstrates micelle size between 10-12 nm. FIG. 2B shows micelle concentration using UV-Vis spectroscopy of free rapamycin, RaM and TRaM identifies rapamycin (275 nm) and Dylight 680 (692 nm). Concentration of each batch calculated based on the rapamycin peak.

FIG. 4A shows confocal microscopic imaging was performed to assess the uptake of both RaM and TRaMs by HUVEC at 6 and 24 hours. HUVEC were incubated with either TRaM or RaM (10 ng/ml and 100 ng/ml) were used at both time points. RaM and TRaM were taken up in a time-dependent fashion. TRaMs appeared to internalize more rapidly than RaMs and were present at higher levels at 24 hrs. FIG. 4B shows mean fluorescence imaging of internalized NPs at 24 hours performed to quantify RaM and TRaM uptake. TRaM (10 or 100 ng/ml) shows a significant increase in fluorescence intensity when compared to the same concentration of RaM and media control (***P<0.001). FIG. 4C shows TRaM accumulates in integrin αVβ3 positive HUVEC after 24 hours. HUVEC nuclei were stained with Hoechst stain and for integrin αVβ3.

DETAILED DESCRIPTION

Figure 1:
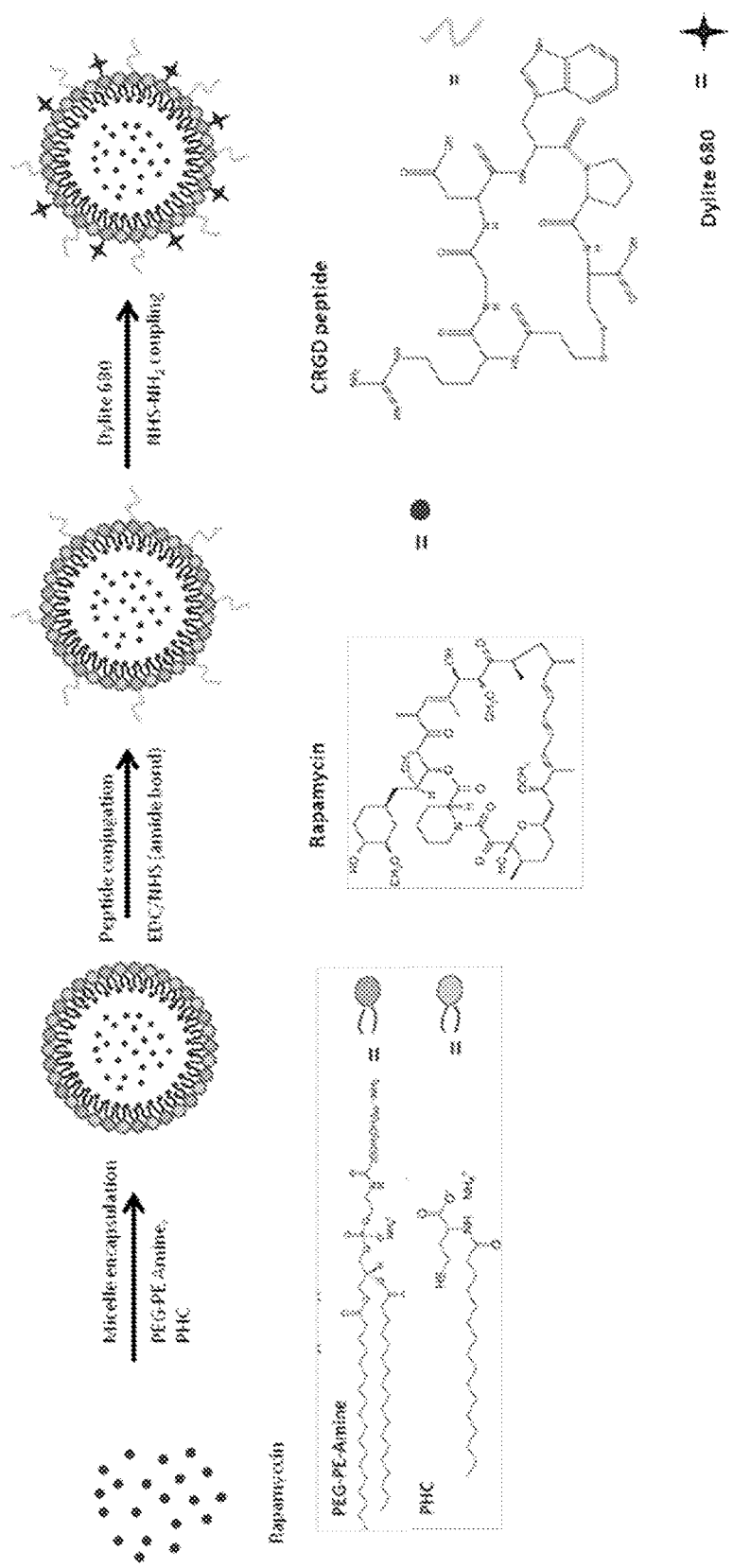
FIG. 1 is schematic representation of Targeted Rapamycin Micelle (TRaM) synthesis. TRaM are composed of rapamycin, NIR fluorophore (Dylight 680), and cRGD peptide targeting moiety for tracking and targeting purposes, respectively.

Immunosuppressive agents are of significant clinical importance. For example, rapamycin (sirolimus), a large (MW 914 g/mol) lipophilic carboxylic lactone-lactam macrolide antibiotic, is recognized for its potent anti-proliferative and immune-suppressive effects in vitro and in vivo. From previous studies, it has been discovered that anti-tumor mechanism of rapamycin operates by binding to FKBP 12 and inhibiting mammalian target of rapamycin (mTOR) Inhibition of mTOR, a vital controller of proliferation, apoptosis and cell growth, initiates cell-cycle seizure in the G1 phase. Despite its promising properties, clinical applications of rapamycin have been limited due to its hydrophobicity, which limits its capacity using routes such as intravenous administrations. Presently, the commercially available formulations of rapamycin include tablet or oral forms. Nevertheless, the low oral bioavailability of rapamycin limits the effectiveness of both of these forms. In addition, the lipophilicity makes the drug susceptible to attachment to lipid membranes of cells nonspecifically thereby reducing its availability to tumor cells and increasing offsite toxicities.

In order to design an efficient and effective drug carrier, a nanocarrier was designed with: (1) a tailored surface to attach biomolecules for targeted drug delivery; (2) a biocompatible coating which can efficiently encapsulate the hydrophobic drug thereby reducing cytotoxicity; and optionally (3) stimuli-induced disruption of the carrier for controlled drug release in the desired environment. Micelles or liposomes are good choice of carrier as they fulfill these requirements based on their composition. Disclosed is a mono-targeted micelle-immunosuppressive agent conjugate delivery system. The potential of this conjugate derives from the physical and chemical protection offered to the conjugate by micelle encapsulation of the drug during its delivery to the transplantation site and release of the drug by micelle breakdown when it is in the immediate vicinity of the organ allograft.

C3 breakdown products have been shown to deposit in cardiac allografts early post-transplantation as a response to ischemia-reperfusion injury, an unavoidable event in all solid organ transplants. By targeting C3 breakdown products, immunosuppressive agents (e.g., mTOR inhibitors such as rapamycin) can be delivered directly to the grafted organ.

C3 activation fragments are abundant complement opsonins found at a site of complement activation, and they serve as ligands for various C3 receptors. One such receptor, Complement Receptor 2 (CR2), a transmembrane protein, plays an important role in humoral immunity by way of its expression predominantly on mature B cells and follicular dendritic cells. CR2 is a member of the C3 binding protein family and consists of 15-16 short consensus repeat (SCR) domains, structural units that are characteristic of these proteins, with the C3 binding site being contained in the two N-terminal SCRs. Natural ligands for CR2 are iC3b, C3dg and C3d, cell-bound breakdown fragments of C3b that bind to the two N-terminal SCR domains of CR2. Cleavage of C3 results initially in the generation and deposition of C3b on the activating cell surface. The C3b fragment is involved in the generation of enzymatic complexes that amplify the complement cascade. On a cell surface, C3b is rapidly converted to inactive iC3b, particularly when deposited on a host surface containing regulators of complement activation. Even in absence of membrane bound complement regulators, substantial levels of iC3b are formed. iC3b is subsequently digested to the membrane bound fragments C3dg and then C3d by serum proteases, but this process is relatively slow. Thus, the C3 ligands for CR2 are relatively long lived once they are generated and will be present in high concentrations at sites of complement activation.

CR2 consists of an extracellular portion consisting of 15 or 16 repeating units known as short consensus repeats (SCRs). Amino acids 1-20 comprise the leader peptide, amino acids 23-82 comprise SCR1, amino acids 91-146 comprise SCR2, amino acids 154-210 comprise SCR3, amino acids 215-271 comprise SCR4. The active site (C3dg binding site) is located in SCR 1-2 (the first 2 N-terminal SCRs). SCR units are separated by short sequences of variable length that serve as spacers. It is understood that any number of SCRs containing the active site can be used. In one embodiment, the construct contains the 4 N-terminal SCR units. In another embodiment, the construct includes the first two N-terminal SCRs. In another embodiment the construct includes the first three N-terminal SCRs. An amino acid sequence for human CR2 is shown below (Accession No. NM_001006658):

```
                                        (SEQ ID NO: 1)
MGAAGLLGVFLALVAPGVLGISCGSPPPILNGRISYYSTPIAVGTVIRYS

CSGTFRLIGEKSLLCITKDKVDGTWDKPAPKCEYFNKYSSCPEPIVPGGY

KIRGSTPYRHGDSVTFACKTNFSMNGNKSVWCQANNMWGPTRLPTCVSVF

PLECPALPMIHNGHHTSENVGSIAPGLSVTYSCESGYLLVGEKIINCLSS

GKWSAVPPTCEEARCKSLGRFPNGKVKEPPILRVGVTANFFCDEGYRLQG

PPSSRCVIAGQGVAWTKMPVCEEIFCPSPPPILNGRHIGNSLANVSYGSI

VTYTCDPDPEEGVNFILIGESTLRCTVDSQKTGTWSGPAPRCELSTSAVQ

CPHPQILRGRMVSGQKDRYTYNDTVIFACMFGFTLKGSKQIRCNAQGTWE

PSAPVCEKECQAPPNILNGQKEDRHMVRFDPGTSIKYSCNPGYVLVGEES

IQCTSEGVWTPPVPQCKVAACEATGRQLLTKPQHQFVRPDVNSSCGEGYK

LSGSVYQECQGTIPWFMEIRLCKEITCPPPPVIYNGAHTGSSLEDFPYGT

TVTYTCNPGPERGVEFSLIGESTIRCTSNDQERGTWSGPAPLCKLSLLAV

QCSHVHIANGYKISGKEAPYFYNDTVTFKCYSGFTLKGSSQIRCKADNTW

DPEIPVCEKGCQSPPGLHHGRHTGGNTVFFVSGMTVDYTCDPGYLLVGNK

SIHCMPSGNWSPSAPRCEETCQHVRQSLQELPAGSRVELVNTSCQDGYQL

TGHAYQMCQDAENGIWFKKIPLCKVIHCHPPPVIVNGKHTGMMAENFLYG

NEVSYECDQGFYLLGEKKLQCRSDSKGHGSWSGPSPQCLRSPPVTRCPNP
```

```
-continued
EVKHGYKLNKTHSAYSHNDIVYVDCNPGFIMNGSRVIRCHTDNTWVPGVP

TCIKKAFIGCPPPPKTPNGNHTGGNIARFSPGMSILYSCDQGYLLVGEAL

LLCTHEGTWSQPAPHCKEVNCSSPADMDGIQKGLEPRKMYQYGAVVTLEC

EDGYMLEGSPQSQCQSDHQWNPPLAVCRSRSLAPVLCGIAAGLILLTFLI

VITLYVISKHRARNYYTDTSQKEAFHLEAREVYSVDPYNPAS.
```

It is understood that species and strain variation exist for the disclosed peptides, polypeptides, proteins, protein fragments and compositions. Specifically disclosed are all species and strain variations for the disclosed peptides, polypeptides, proteins, protein fragments and compositions.

Also disclosed are compositions, wherein the construct is a fusion protein. Herein a "fusion protein" means two or more components comprising peptides, polypeptides, or proteins operably linked. CR2 can be linked to complement inhibitors or activators by an amino acid linking sequence. Examples of linkers are well known in the art. Examples of linkers can include but are not limited to (Gly4Ser)3 (G4S), (Gly3Ser)4 (G3S), SerGly4, and SerGly4SerGly4. Linking sequences can also consist of "natural" linking sequences found between SCR units within human (or mouse) proteins, for example VSVFPLE, the linking sequence between SCR 2 and 3 of human CR2. Fusion proteins can also be constructed without linking sequences.

In some embodiments, the agent that binds C3 breakdown products is coupled to a complement inhibitor. There are two broad classes of membrane complement inhibitor; inhibitors of the complement activation pathway (inhibit C3 convertase formation), and inhibitors of the terminal complement pathway (inhibit MAC formation). Membrane inhibitors of complement activation include Complement Receptor 1 (CR1), decay-accelerating factor (DAF) and membrane cofactor protein (MCP). They all have a protein structure that consists of varying numbers of repeating units of about 60-70 amino acids termed short consensus repeats (SCR) that are a common feature of C3/C4 binding proteins. Rodent homologues of human complement activation inhibitors have been identified. The rodent protein Crry is a widely distributed inhibitor of complement activation that functions similar to both DAF and MCP. Rodents also express DAF and MCP, although Crry appears to be functionally the most important regulator of complement activation in rodents. Although there is no homolog of Crry found in humans, the study of Crry and its use in animal models is clinically relevant.

Control of the terminal complement pathway and MAC formation in host cell membranes occurs principally through the activity of CD59, a widely distributed 20 kD glycoprotein attached to plasma membranes by a glucosylphosphatidylinositol (GPI) anchor. CD59 binds to C8 and C9 in the assembling MAC and prevents membrane insertion.

Various types of complement inhibitory proteins are currently under investigation for therapy of inflammatory disease and disease states associated with bio-incompatibility. Two of the best therapeutically characterized inhibitors of human complement are a soluble form of Complement Receptor 1 (sCR1) and an anti-C5 monoclonal antibody. These systemically active inhibitory proteins have shown efficacy in various animal models of disease and more recently in clinical trials. Anti-C5 mAb inhibits the generation of C5a and the MAC, whereas sCR1 is an inhibitor of complement activation and also inhibits the generation of C3 activation products. Soluble forms of human DAF and MCP, membrane inhibitors of complement activation, have also been shown to be protective an animal models of inflammation and bio-incompatability. CD59 is a membrane inhibitor of complement that blocks assembly of the MAC, but does not affect generation of complement opsonins or C3a and C5a. Soluble forms of CD59 have been produced, but its low functional activity in vitro, particularly in the presence of serum, indicates that sCD59 will have little or no therapeutic efficacy.

Constructs containing CR2 linked to complement inhibitors are described in U.S. Pat. No. 8,007,804 to Tomlinson et al., and U.S. Pat. No. 8,540,997 to Tomlinson et al., which are hereby incorporated by references in their entirety for the teaching of these constructs.

In some embodiments, the surface agent comprises a peptide or peptidomimetic that binds an integrin. For example, a polypeptide comprising the amino acid sequence Arg-Gly-Asp (RGD) is capable of binding integrins. As used herein, the term "RDG sequence", "RGD peptide", or "RGD compound" means a molecule having at least one Arg-Gly-Asp sequence that functions to bind an integrin molecule, such as αvβ3. As used herein, the term "cyclic RGD sequence" or "cyclic RGD molecule" means a cyclic sequence or molecule comprising an "RGD sequence" as defined above.

Integrin receptors can bind a variety of RGD sequences of variety lengths (see, for example, Ruoslahti et al., In Morphoregulatory Molecules, G. M. Edelman et al., eds. (1990); Ruoslahti, J. Chin. Invest. 87:1-5 (1991)). Thus, it is intended that the length of an RGD peptide can vary, for example, from four amino acids up to 100 amino acids or more. For example, the RGD peptide can be from about 5 to about 50 amino acids, such as from about 6 to about 25 amino acids. Moreover, it is recognized that the amino acids or other entities that flank the RGD sequence can vary without destroying activity of the molecule. As such, variation of flanking amino acids are specifically contemplated, so long as the variant does not completely lose its activity.

Additionally, it is intended that the RGD sequence includes any compound having an amino acid sequence that is functionally equivalent to the sequence Arg-Gly-Asp. For example, one skilled in the art will recognize that substitution of amino acids can be made using non-natural or synthetic amino acids that result in a peptide having similar or equivalent functionality. Other examples of functional RGD equivalents include amino acid derivatives and mimics described, for example, in U.S. Pat. Nos. 5,612,311 and 5,858,972, which are incorporated herein by reference.

The RGD peptide can be linear or cyclic. In some embodiments, the surface agent comprises a cyclized arginine-glycineaspartic acid (cRGD). Cyclic or conformationally constrained RGD molecules are described, for example, in U.S. Pat. Nos. 5,547,936; 5,827,821; 5,672,585; 5,627,263 and 5,912,234, which are incorporated herein by reference. Such cyclic RGD molecules having disulfide linkages or other intramolecular bonds in various positions relative to the RGD motif can be used.

The nanocarrier can be any suitable vehicle for the delivery of active agents, including non-targeting and targeting. A variety of suitable nanocarriers are known in the art, and include for example micelles, solid nanoparticles, and liposomes.

In some embodiments, the nanocarrier can include a polymeric nanoparticle. For example, the nanocarrier can comprise one or more polymeric matrices. The nanocarrier can also include other nanomaterials and can be, for example, lipid-polymer nanoparticles. In some embodiments, a polymeric matrix can be surrounded by a coating layer (e.g., liposome, lipid monolayer, micelle, etc.). Examples of classes of nanocarriers that can be adapted (e.g., by incorporation of a suitable surface agent) to deliver immunosuppressive agents include (1) biodegradable nanoparticles, such as those described in U.S. Pat. No. 5,543,158 to Gref et al., (2) polymeric nanoparticles such as those described in U.S. Pat. No. 7,534,448 to Saltzman et al., (3) lithographically constructed nanoparticles, such as those described in U.S. Pat. No. 8,420,124 to DeSimone et al., (4) nanoparticles such as those described in U.S. Patent Application Publication No. 2010/0233251 to von Andrian et al., or (5) nanoparticles such as those described in U.S. Pat. No. 7,364,919 to Penades et al.

In some cases, release of the immunosuppressive agent (e.g., an mTOR inhibitor such as rapamycin or a derivative thereof) is triggered by the decrease in endosomal pH initiated by cellular uptake. The encapsulated immunosuppressive agent is then delivered at the level of the graft. Recent data suggests that rapamycin may impede the emigration of passenger leukocytes to lymphoid organs, confirming that the release of rapamycin at the level of the organ itself may blunt allo-immune responses. Accordingly, in some embodiments, the nanocarrier can be a nanocarrier which is pH sensitive so as to provide for the pH triggered release of the immunosuppressive agent. The term "pH triggered release" is intended to mean that the rate of release of the immunosuppressive agent from the nanocarrier is dependent on or regulated by the pH of the media or environment surrounding the nanocarrier.

For example, the nanocarrier can be a micelle or liposome that comprises N-palmitoyl homocysteine (PHC). Other pH sensitive lipids include:

1) N-(4-carboxybenzyl)-N,N-dimethyl-2,3-bis (oleoyloxy)propan-1-aminium (DOBAQ)

pH sensitive nanocarriers are known in the art. See, for example, U.S. Patent Application Publication No. 2004/0234597 to Shefer et al. and U.S. Patent Application Publication No. 2010/0303850 to Lipford et al. Suitable pH sensitive nanocarriers can be formed from materials that are pH sensitive provided that the resulting nanocarriers provide for delivery of the immunosuppressive agent at the desired pH. For example, suitable pH sensitive nanocarriers include nanocarriers that provide for the release of one or more encapsulated immunosuppressive agents at a threshold pH of about 6.8 or less (e.g., about 6.5 or less, about 6 or less, or about 5.5 or less).

Such synthetic nanocarriers are well known in the art and include polyketal nanocarriers, pH sensitive liposomes, pH sensitive micelles, polymeric nanoparticles derived from amphiphilic block copolymers, and core-shell materials formed from a core material (e.g., a hydrophobic or hydrophilic core material such as a polymer) and a pH sensitive shell (see for example, U.S. Patent Application Publication No. 2004/0234597 to Shefer et al.).

In some embodiments, the pH sensitive nanocarrier can be a core-shell nanoparticle comprising a hydrophobic core material (e.g., a wax, a fat material such as a lipid, or a hydrophobic polymer) surrounded by a pH sensitive shell material.

In some embodiments, the pH sensitive nanocarrier can be a nanoparticle or micelle formed from an amphiphilic material, such as an amphiphilic block copolymer derived from a hydrophilic polymer segment and a hydrophobic polymer segment. By way of example, the pH sensitive nanocarrier can be a nanoparticle or micelle formed an amphiphilic block copolymer derived from a poly(alkylene oxide) segment (e.g., a polyethylene glycol (PEG) segment) and an aliphatic polyester segment. The aliphatic polyester 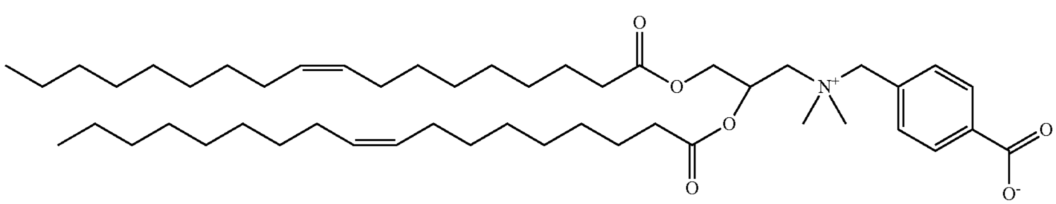 [SMILES: CCCCCCCC/C=C\CCCCCCCC(=O)OCC(C[N+](C)(C)Cc1ccc(C(=O)[O-])cc1)OC(=O)CCCCCCC/C=C\CCCCCCCC] 2) 1,2-dipalmitoyl-sn-glycero-3-succinate (DGS)

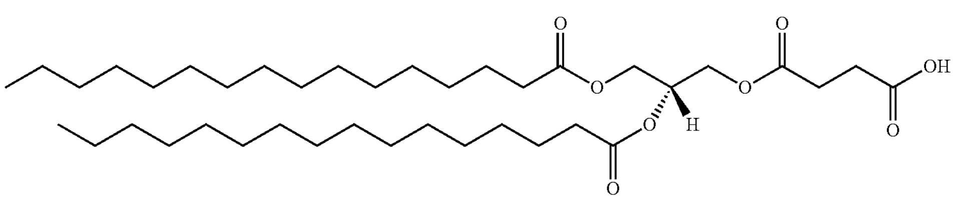 [SMILES: CCCCCCCCCCCCCCCC(=O)OC[C@H](COC(=O)CCC(=O)O)OC(=O)CCCCCCCCCCCCCCC]

These lipids can be used instead of PHC (N-palmitoyl homocysteine) in combination with PEG-PE amine. These molecules are zwitterionic in nature and are affected by pH changes of cellular milieu.

In some embodiments, liposome can be created with a mPEG-Hz-CHEMS. mPEG-Hz-CHEMS has a pH sensitive hydrazone linkage which breaks at around endosomal pH (approximately pH5.5).

segment can be a biodegradable aliphatic polyester, such as poly(lactic acid), poly(glycolic acid), or poly(lactic acid-co-glycolic acid).

In some embodiments, the pH sensitive nanocarrier can be a nanoparticle or micelle or liposome formed from amphiphilic molecule comprising a hydrophilic polymer segment (e.g., a poly(alkylene oxide) segment such as a PEG segment) and a lipid moiety. The lipid moiety can be conjugated to a terminus of the PEG segment, so as to afford a suitable amphiphile. Suitable lipid moieties are known in the art, and include, for example, mono-, di and triglycerides (e.g., glyceryl monostearate or glyceryl tristearate), phospholipids, sphingolipids, cholesterol and steroid derivatives, terpenes and vitamins. In some embodiments, the lipid moiety can be a phospholipid. Suitable phospholipids include, but are not limited to, phosphatidic acids, phosphatidylcholines with both saturated and unsaturated lipids, phosphatidyl ethanolamines, phosphatidylglycerols, phosphatidylserines, phosphatidylinositols, lysophosphatidyl derivatives, cardiolipin, and beta-acyl-y-alkyl phospholipids. In certain embodiments, the pH sensitive nanocarrier can be a nanoparticle or micelle formed from amphiphilic molecule comprising a hydrophilic polymer segment (e.g., a poly(alkylene oxide) segment such as a PEG segment) and a phospholipid moiety.

In some embodiments, the targeted nanocarrier has a mean diameter of 1 nm to 100 nm to optimize vascular permeability and penetration into tissue and cells. In addition with its multifunctional character (large surface area due to small size, surface can be tailored with different functionalities), the nanocarrier behaves like a stealth agent and can evade immune response from the host system due to surface modifications including pegylation.

In some embodiments, the nanocarrier is conjugated with a near-infrared fluorophore, such as DyLight 680, Dylight 755, or IR-800. These fluorophores aid in noninvasive in vivo imaging for the detection of the graft site and monitoring of drug release. In some embodiments, the imaging reporter can be gadolinium, iron oxide, or radioisotopes to monitor delivery of the nanocarrier. In some embodiments, the imaging reporter is an enzyme, such as luciferase or beta-galactosidase.

Nanocarriers can include one or more immunosuppressive agents. Immunosuppressive agents are agents that inhibit, slow, or reverse the activity of the immune system. Immunosuppressive agents act by suppressing the function of responding immune cells (including, for example, T cells), directly (e.g., by acting on the immune cell) or indirectly (by acting on other mediating cells), immunosuppressive agents can be given to a subject to prevent the subject's immune system from mounting an immune response after an organ transplant or for treating a disease that is caused by an overactive immune system.

A number of immunosuppressive agents are known in the art, and include, for example, calcineurin inhibitors (e.g., cyclosporin (CsA) and derivatives thereof; ISA(TX) 247, and tacrolimus (FK-506) and derivatives thereof); azathioprine (AZ); mycophenolate mofetil (MMF); mizoribine (MZ); leflunomide (LEF); adrenocortical steroids (also known as adrenocortical hormones, corticosteroids, or corticoids) such as prednisolone and methylprednisolone; sirolimus (also known as rapamycin); everolimus; FK778; TAFA-93; deoxyspergualin (DSG); FTY720 (chemical name: 2-amino-2-[2-(4-octylphenyl)ethyl]-1,3-propanediol hydrochloride); cyclophosphamide; 15-deoxyspergualin (Gusperimus); interferons; sulfasalazine; mimoribine, misoprostol, anti-IL-2 receptor antibodies, thalidomide, anti-tumor necrosis factor antibodies, anti-CD2 antibodies, anti-CD-147 antibodies, anti-CD4 antibodies, anti-CD8 antibodies, anti-thymocyte globulin antibodies, interleukin-2 α-chain blockers (e.g., basiliximab and daclizumab); inhibitors of inosine monophosphate dehydrogenase (e.g., mycophenolate mofetil); and inhibitors of dihydrofolic acid reductase (e.g., methotrexate).

In some cases, the immunosuppressive agent can include one or more calcineurin inhibitors. Calcineurin inhibitors include drugs or compounds that result in inhibition or down regulation of the biological activity associated with the calcineurin, or of the calcineurin-NFATc pathway, the calcineurin-cofilin pathway or the calcineurin-BAD pathway. Calcineurin inhibitors are known in the art, and include, for example, cyclosporines including cyclosporine A (CsA) and derivatives thereof such as voclosporin (ISA 247), and tacrolimus (FK-506) and derivatives thereof such as pimecrolimus.

In certain embodiments, the immunosuppressive agent can include a cyclosporine. Cyclosporines are fungal metabolites that comprise a class of cyclic oligopeptides that act as immunosuppressants. Cyclosporine A, the structure of which is included below, is a hydrophobic cyclic polypeptide consisting of eleven amino acids. It binds and forms a complex with the intracellular receptor cyclophilin. The cyclosporine/cyclophilin complex binds to and inhibits calcineurin, a $Ca^{2+}$-calmodulin-dependent serine-threonine-specific protein phosphatase. Calcineurin mediates signal transduction events required for T-cell activation. Cyclosporines and their functional and structural derivatives suppress the T cell-dependent immune response by inhibiting antigen-triggered signal transduction. This inhibition decreases the expression of proinflammatory cytokines, such as IL-2. Cyclosporines are highly hydrophobic and readily precipitate in the presence of water (e.g. on contact with body fluids).

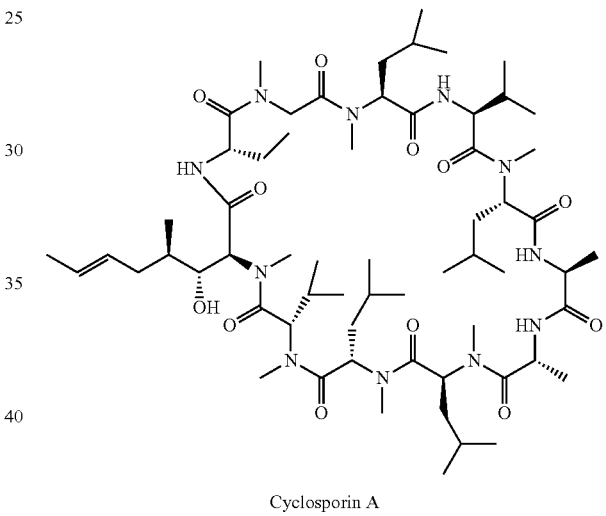

Cyclosporin A

Many different cyclosporines (e.g., cyclosporine A, B, C, D, E, F, G, H, and I) are produced by fungi. Cyclosporine A is commercially available under the trade name NEORAL® from Novartis. Cyclosporine A structural and functional derivatives include cyclosporines having one or more fluorinated amino acids (described, e.g., in U.S. Pat. No. 5,227,467); cyclosporines having modified amino acids (described, e.g., in U.S. Pat. Nos. 5,122,511 and 4,798,823); and deuterated cyclosporines, such as ISAtx247 (described in U.S. Patent Application Publication No. 2002/0132763 A1).

Additional cyclosporine derivatives are described in U.S. Pat. Nos. 6,136,357, 4,384,996, 5,284,826, and 5,709,797. Cyclosporine derivatives include, but are not limited to, D-Sar (α-SMe)³ Val²-DH-Cs (209-825), Allo-Thr-2-Cs, Norvaline-2-Cs, D-Ala(3-acetylamino)-8-Cs, Thr-2-Cs, and D-MeSer-3-Cs, D-Ser(O—$CH_2CH_2$— OH)-8-Cs, and D-Ser-8-Cs, which are described in Cruz et al. (Antimicrob. Agents Chemother. 44: 143-149, 2000).

In some embodiments, the immunosuppressive agent includes cyclosporine A.

In some embodiments, the immunosuppressive agent includes a derivative of cyclosporine A, such as voclosporin, the structure of which is shown below.

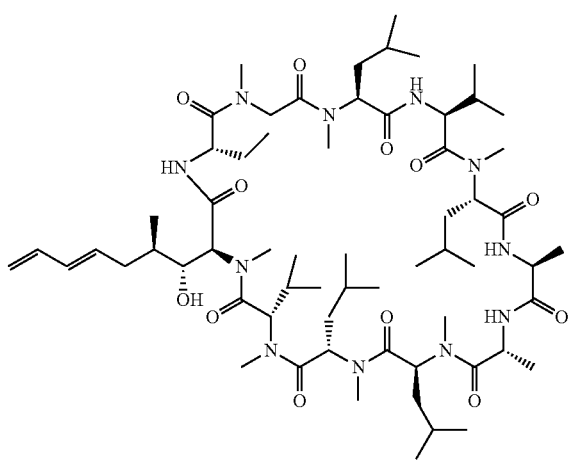 [SMILES: C=C/C=C/C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

In certain embodiments, the immunosuppressive agent can include tacrolimus or a derivative thereof. Tacrolimus (FK506 or Fujimycin) is an immunosuppressive agent that targets T cell intracellular signal transduction pathways. Tacrolimus binds to an intracellular protein FK506 binding protein (FKBP-12) that is not structurally related to cyclophilin. The FKBP/FK506 complex binds to calcineurin and inhibits calcineurin's phosphatase activity. This inhibition prevents the dephosphorylation and nuclear translocation of nuclear factor of activated T cells (NFAT), a nuclear component that initiates gene transcription required for proinflammatory cytokine (e.g., IL-2, gamma interferon) production and T cell activation. Thus, tacrolimus inhibits T cell activation.

Tacrolimus, the structure of which is included below, is a 23-membered macrolide lactone discovered in 1984 from the fermentation broth of a Japanese soil sample that contained the bacteria *Streptomyces tsukubaensis*. Formulations including tacrolimus are commercially available under the trade names PROGRAF®, ADVAGRAF®, and PROTOPIC® from Astellas Pharma.

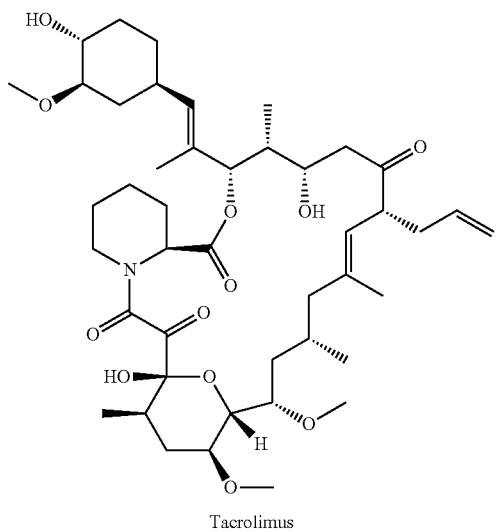 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

Tacrolimus

Tacrolimus and tacrolimus derivatives are known in the art, and are described, for example, in U.S. Pat. Nos. 4,894,366, 4,929,611, and 4,956,352. By way of example, FK506-related compounds, including ascomycin (FR-900520), FR-900523, and FR-900525, are described in U.S. Pat. No. 5,254,562; O-aryl, O-alkyl, O-alkenyl, and O-alkynyl macrolides are described in U.S. Pat. Nos. 5,250,678, 532,248, 5,693,648; amino O-aryl macrolides are described in U.S. Pat. No. 5,262,533; alkylidene macrolides are described in U.S. Pat. No. 5,284,840; N-heteroaryl, N-alkylheteroaryl, N-alkenylheteroaryl, and N-alkynylheteroaryl macrolides are described in U.S. Pat. No. 5,208,241; aminomacrolides and derivatives thereof are described in U.S. Pat. No. 5,208,228; fluoromacrolides are described in U.S. Pat. No. 5,189,042; amino O-alkyl, O-alkenyl, and O-alkynyl-macrolides are described in U.S. Pat. No. 5,162,334; and halomacrolides are described in U.S. Pat. No. 5,143,918. Pimecrolimus, another tacrolimus derivative, is a 33-epichloro derivative of ascomyin. Pimecrolimus structural and functional derivatives are described, for example, in U.S. Pat. No. 6,384,073.

In some embodiments, the immunosuppressive agent includes tacrolimus.

In some embodiments, the immunosuppressive agent includes ascomycin, the structure of which is shown below.

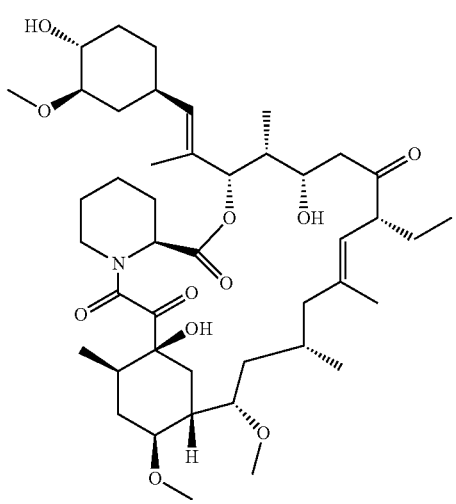 [SMILES: CC[C@@H]1/C=C(\C)C[C@H](C)C[C@H](OC)[C@H]2C[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

In some embodiments, the immunosuppressive agent includes pimecrolimus, the structure of which is shown below.

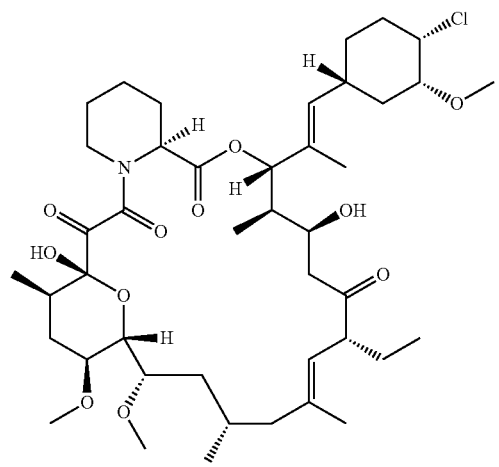

In some cases, the immunosuppressive agent can include one or more mTOR inhibitors. mTOR inhibitors include compounds or ligands, or pharmaceutically acceptable salts thereof, which inhibit cell replication by blocking the progression of the cell cycle from G1 to S through the modulation of mTOR activity or expression. A number of mTOR inhibitors are commercially available or under development, including rapamycin (sirolimus, marketed under the trade name RAPAMUNE® by Wyeth), temsirolimus (TORISEL®; Wyeth), everolimus (also known as RAD001; marketed under the trade names ZORTRESS® and AFINITOR® by Novartis), ridaforolimus (also known as deforolimus, AP23573, and MK-8669, being developed by Merck and ARIAD pharmaceuticals), TOP216 (Toptarget A/S), OSI-027 (OSI Pharma), TAFA93 (Isotechnika), nab-rapamycin (APP Phama), and merilimus.

In some embodiments, the pharmaceutical composition contains rapamycin (sirolimus, marketed under the trade name RAPAMUNE® by Wyeth), the structure of which is shown below.

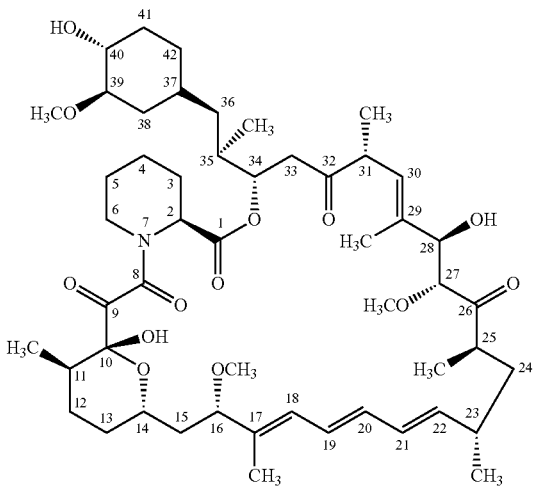

Rapamycin is a macrolide produced by *Streptomyces hygroscopicus*. Rapamycin is a potent immunosuppressive agent, and is used clinically to prevent rejection of transplanted organs.

In some embodiments, the pharmaceutical composition contains a rapamycin derivative. Rapamycin derivatives include compounds that are chemically or biologically modified derivatives of the rapamycin nucleus which retain activity as mTOR inhibitors. The term "rapamycin nucleus", as used herein, refers to the macrolide ring structure shown below.

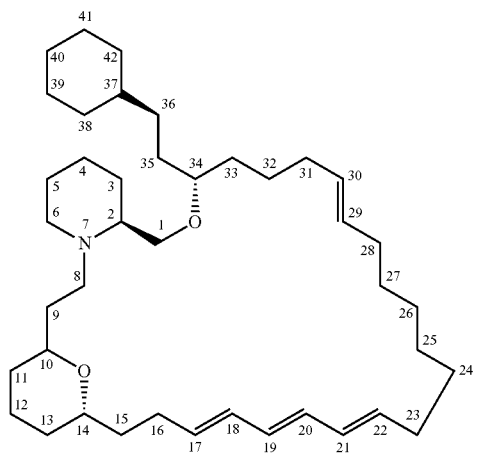

Examples of rapamycin derivatives include esters, ethers, carbamates, oximes, hydrazones, and hydroxylamines of rapamycin, as well as compounds in which one or more of the functional groups attached to the attached to the rapamycin nucleus have been modified, for example, through reduction or oxidation.

Suitable rapamycin derivatives include rapamycin derivatives containing a substitution at the C-40 position of rapamycin. If the C-40 substituent is designated as R, then the following substitutions and corresponding suitable compounds are: R=—OP(O)(Me)$_2$, AP23573 (International Patent Publication Nos. WO 98/02441 and WO 2001/14387); R=—OC(O)C(CH$_3$)(CH$_2$OH), temsirolimus (U.S. Pat. No. 5,362,718); R=—OCH$_2$CH$_2$OH, everolimus (U.S. Pat. No. 5,665,772); R=—OCH$_2$CH$_2$OEt, biolimus; R=-tetrazole, zotarolimus or ABT-578 (International Patent Publication No. WO 99/15530); and R=—Cl, pimecrolimus.

Other suitable rapamycin derivatives include rapamycin derivatives including substitutions in the C-40 and/or C-16 and/or C-32 positions. Esters and ethers of rapamycin are described in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. Nos. 5,118,678; 5,411,967; 5,434,260; 5,480,988; 5,480,989; 5,489,680); silyl esters (U.S. Pat. No. 5,120,842); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); amidino carbamate esters (U.S. Pat. No. 5,463,048); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462); 32-esters and ethers (U.S. Pat. No. 5,256,790). Other suitable rapamycin derivatives include oximes, hydrazones, and hydroxylamines of rapamycin as disclosed in U.S. Pat. Nos. 5,373,014, 5,378,836, 5,023,264, and 5,563,145. 40-oxorapamycin, another suitable rapamycin derivative, is disclosed in U.S. Pat. No. 5,023,263.

In certain embodiments, the immunosuppressive agent includes an mTOR inhibitor defined by the following general formula

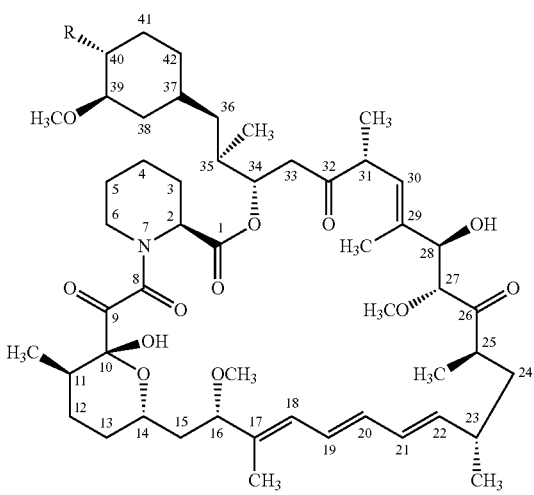

wherein R is —OH, —OP(O)(Me)$_2$, —OC(O)C(CH$_3$)(CH$_2$OH), —Cl, —OCH$_2$CH$_2$OCH$_2$CH$_3$, or a tetrazole ring.

In certain embodiments, the immunosuppressive agent includes rapamycin, the structure of which is shown below.

In certain embodiments, the immunosuppressive agent includes temsirolimus, the structure of which is shown below.

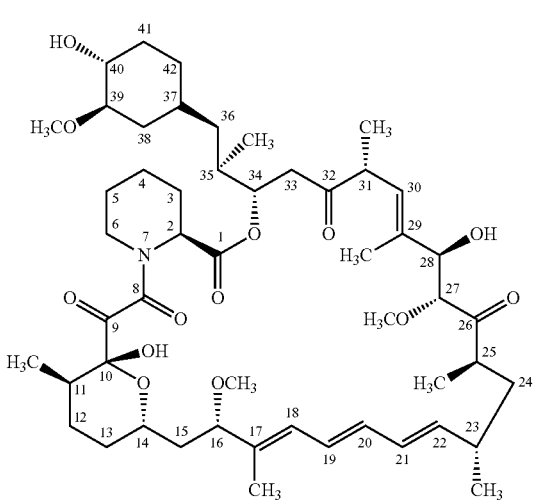

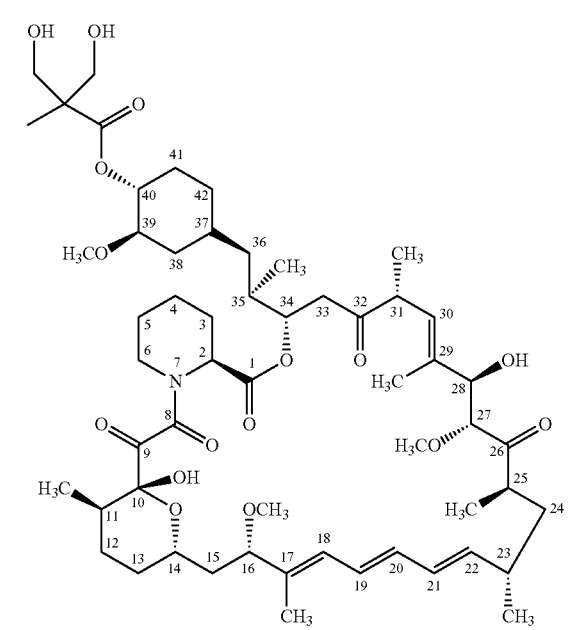

In certain embodiments, the immunosuppressive agent includes everolimus, the structure of which is shown below.

In certain embodiments, the immunosuppressive agent includes biolimus, the structure of which is shown below.

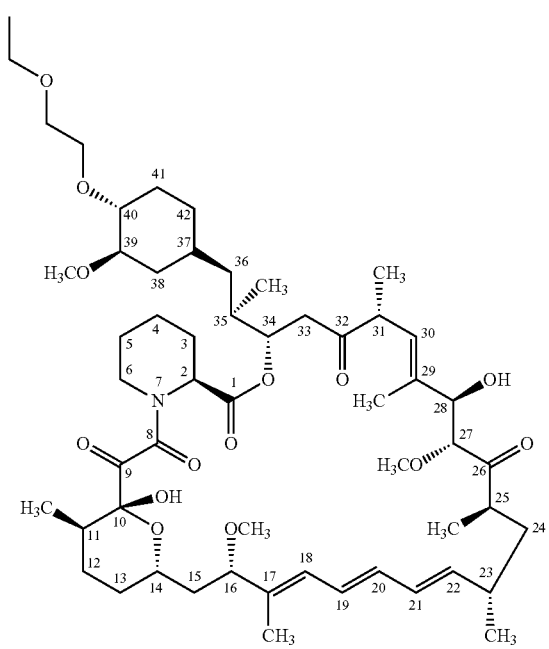

In certain embodiments, the immunosuppressive agent includes zotarolimus, the structure of which is shown below.

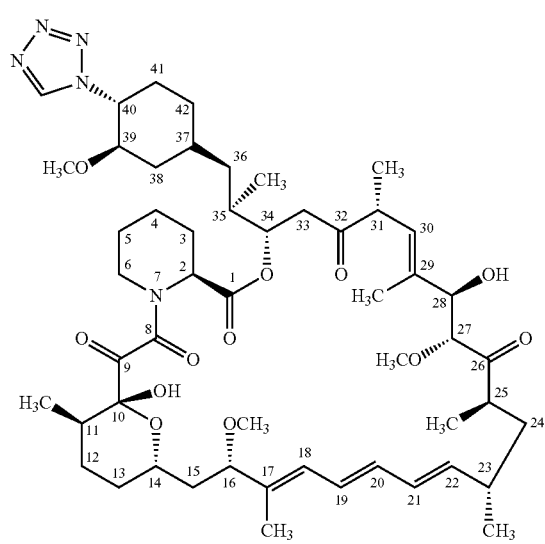

In certain embodiments, the immunosuppressive agent includes ridaforolimus, the structure of which is shown below.

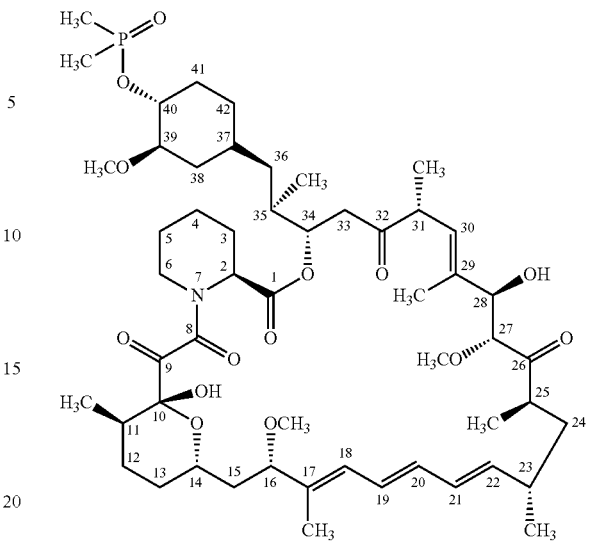

In certain embodiments, the immunosuppressive agent includes the rapamycin derivative shown below.

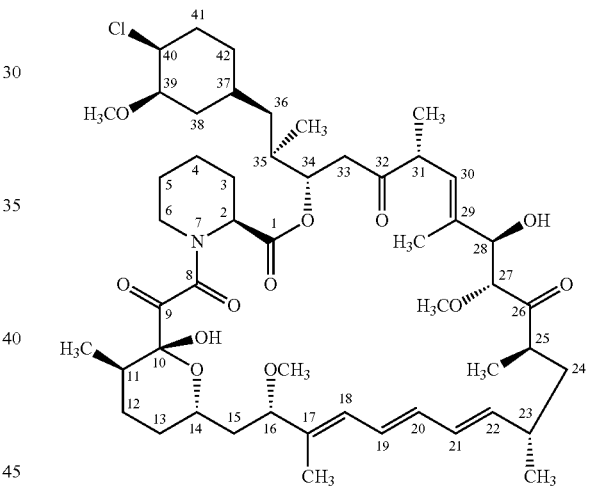

Other suitable immunosuppressive agents include small molecule inhibitors of mTOR, including fused bicyclic compounds (such as those described in International Patent Publication Nos. WO 2007/61737, WO 2007/87395, WO 2007/64993, and U.S. Patent Application Publication No. US 2007/0112005), heteroaromatic amines (such as those described in International Patent Publication No. WO 2001/19828), pyrrolopyrimidine compounds (such as those described in International Patent Publication No. WO 2005/47289), diphenyl-dihydro-indol-2-one derivatives (such as those described in International Patent Publication No. WO 2005/97107), and trimethydodeca-triene derivatives (such as those described in US Patent Publication No. 2007/037887). Also suitable are dual PI3K/mTOR kinase inhibitors, such as the compound PI-103, as described in Fan, Q-W, et al. *Cancer Cell* 9:341-349 (2006) and Knight, Z. A. et al. *Cell* 125:733-747 (2006).

The immunosuppressive agent can also be a pharmaceutically acceptable prodrug of an immunosuppressive agent, for example a prodrug of an mTOR inhibitor such as rapamycin or a rapamycin derivative. Prodrugs are compounds that, when metabolized in vivo, undergo conversion to compounds having the desired pharmacological activity (e g, immunosuppressive activity). Prodrugs can be prepared by replacing appropriate functionalities present in immunosuppressive agent with "pro-moieties" as described, for example, in H. Bundgaar, Design of Prodrugs (1985). Examples of prodrugs include ester, ether or amide derivatives of the immunosuppressive agents described herein, and their pharmaceutically acceptable salts. For further discussions of prodrugs, see, for example, T. Higuchi and V. Stella "Pro-drugs as Novel Delivery Systems," ACS Symposium Series 14 (1975) and E. B. Roche ed., Bioreversible Carriers in Drug Design (1987).

The immunosuppressive agent can also be a pharmaceutically acceptable salt of an immunosuppressive agent, such as a salt of an mTOR inhibitor such as rapamycin or a rapamycin derivative. In some cases, it may be desirable to prepare a formulation containing a salt of an immunosuppressive agent due to one or more of the salt's advantageous physical properties, such as enhanced stability or a desirable solubility or dissolution profile.

Generally, pharmaceutically acceptable salts of immunosuppressive agents can be prepared by reaction of the free acid or base forms of the immunosuppressive agent with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found, for example, in Remington's Pharmaceutical Sciences, 20th ed., Lippincott Williams & Wilkins, Baltimore, Md., 2000, p. 704.

Suitable pharmaceutically acceptable acid addition salts of immunosuppressive agent, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids.

Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

In some cases, the pharmaceutically acceptable salt of an immunosuppressive agent may include alkali metal salts, including but not limited to sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

Formulations can also contain a pharmaceutically acceptable clathrate of an immunosuppressive agent, such as a clathrate of an mTOR inhibitor such as rapamycin or a rapamycin derivative. Clathrates are drug-host inclusion complexes formed when a drug is associated with or in a host molecule or molecules in stoichiometric ratio. For example, rapamycin or rapamycin derivatives can form inclusion complexes with cyclodextrins or other host molecules.

Many immunosuppressive agents, for example mTOR inhibitors such as rapamycin and derivatives of rapamycin, as well as pharmaceutically acceptable prodrugs or salts thereof, may contain one or more chiral centers, and thus exist as one or more stereoisomers. Such stereoisomers can be prepared and/or isolated as a single enantiomer, a mixture of diastereomers, or a racemic mixture. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

The disclosed targeted nanocarriers can be used therapeutically in combination with a pharmaceutically acceptable carrier. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Disclosed is a method for suppressing an allo-immune response in a subject, such as one that can occur after an allograft transplantion. The method can comprise administering to the subject before, during, or after an allograft transplantation an effective amount of composition comprising an immunosuppressive agent (e.g., an mTOR inhibitor such as rapamycin or a rapamycin derivative) encapsulated in a nanocarrier that specifically targets C3 breakdown products, integrin, or a combination thereof. For example, the method can comprise administering any of the targeted nanocarriers disclosed herein.

Cellular therapies including the use of particular subsets of CD4+ T cells expressing the markers CD25hi CD127lo FOXP3+ have been termed "regulatory T cells (Treg)" for their innate suppressive capacity. These Treg have enjoyed much attention in the literature for their natural and adaptive ability to suppress allo-immune responses and provide long-term graft survival in various mouse and humanized experimental models. Harnessing the suppressive capacity of Treg and applying them to the clinic is under vigorous investigation at present, and is now in early stages of clinical trials. Additionally, various pharmacotherapeutics have been shown to bolster the natural suppressive capacity of these Treg. Therefore, the method can also comprise administering to the subject a composition comprising regulatory T cells (Treg).

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

The term "subject" refers to any individual who is the target of administration or treatment. The subject can be a vertebrate, for example, a mammal Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" or "suppress" refers to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, or 95% homology to a reference sequence.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e g immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "residue" as used herein refers to an amino acid that is incorporated into a polypeptide. The amino acid may be a naturally occurring amino acid and, unless otherwise limited, may encompass known analogs of natural amino acids that can function in a similar manner as naturally occurring amino, acids.

The term "position," with respect to an amino acid residue in a polypeptide, refers to a number corresponding to the numerical place that residue holds in the polypeptide. By convention, residues are counted from the amino terminus to the carboxyl terminus of the polypeptide.

A "fusion protein" refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides or it may be expressed as a single polypeptide from nucleic acid sequence encoding the single contiguous fusion protein. A single chain fusion protein is a fusion protein having a single contiguous polypeptide backbone.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Immunosuppressive Nanotherapeutic Micelles Blunt Endothelial Cell Inflammation and Immunogenicity in Models of Transplantation Methods Cell Culture Human Umbilical Vein Endothelial Cells (HUVEC), complete endothelial growth medium-2 (EGM-2) and bullet kit were purchased from Lonza (Walkersville, Md.). Cells were grown and maintained in a humidified 37° C. and 5% $CO_2$ atmosphere. Cells were expanded on T75 $cm^2$ polystyrene flasks to passage 5 and plated onto 6-well plates for experimental assays (Fischer Scientific, Pittsburgh, Pa.).

Synthesis of Micelle-Encapsulated Rapamycin

Micelle encapsulation of rapamycin (RaM) was carried out as described by Dubertret et al (Ponticelli, C. Journal of nephrology 17:762-768 (2004)). Typically, rapamycin was mixed with 2.5 mg of amino-PEG-PE (1,2-diacyl-snglycero-3-phosphoethanolamine-N-[amino-poly(ethylene glycol)] and 0.5 mg of PHC (N-palmitoyl homocysteine (ammonium salt)), suspended in chloroform and the solvent was evaporated in a vacuum oven at room temperature. Lipids were purchased from Avanti Polar Lipids (AL). The pellet obtained after evaporation was heated to 80° C. and dissolved in nanopure water to produce amine functionalized micelles. The micelle solution was sonicated for 1 hour in a water bath and filtered using a 0.2 µm syringe filter to remove aggregates. For the synthesis of TRaM, the RaM solution was used for peptide conjugation (1:1 ratio of carboxyl group on peptide to amine group on the micelles at 30% coverage of amines). After 15 minutes of incubation at room temperature, PBS (pH~12) was added to bring the pH back to 7.5. The micelle solution was added to the peptide solution and incubated for 2 hours at room temperature. After 2 hours, excess peptide was purified using 10K MWCO ultracentrifugal device (Millipore, MD) at 4000 rpm for 15 minutes at 4° C. For dye labeling, RaM and TRaM solutions were added to NHS Dylight 680 (ratio of covering 30% amines on the micelles), respectively. The solution was incubated for 1 hour at room temperature. Excess dye was purified using 10K MWCO ultracentrifugal device at 4000 rpm for 15 minutes at 4° C.

Characterization of Micelle-Encapsulated Rapamycin

Dynamic Light Scattering (DLS) of micelles in aqueous solution was performed on a ZetaPALS particle analyzer (Brookhaven Instruments, NY). The respective aqueous master solution was diluted and sonicated to prevent aggregation. The solution was filtered using a 0.2 µm syringe filter before taking the measurements. The concentrations of each micelle batch were determined by UV-Vis absorption using a Biotek microplate spectrophotometer (VT). For pH change experiments, PBS buffers of pH 4-9 were prepared. RaM or TRaM-cRGD (approximately $10^{-4}$ M) were placed in a 96 well plate. PBS buffers of increasing pH were added to respective wells. The wells were incubated for 4 hours. After 4 hours, UV-Vis measurements were recorded at 275 nm (rapamycin excitation).

In Vitro Treatments with Encapsulated Rapamycin

Cells were plated at consistent densities of $1-2 \times 10^5$ cells/well and grown to confluence. A 1 mg/mL stock solution of rapamycin (Sigma-Aldrich, WI) and dimethyl sulfoxide (DMSO) was prepared and stored at 4° C. The stock solution was used to prepare free rapamycin solutions and NPs as described previously. Targeted NPs, untargeted NPs, and free rapamycin were diluted in EGM-2 media to 10 and 100 ng/mL concentrations. Cells were pre-incubated with 0.01% DMSO vehicle, EGM-2 media, free rapamycin, or NPs for 1 hour. Cells were washed two times with 0.02% Bovine Serum Albumin diluted in Hanks Balanced Salt Solution (HBSS/BSA wash solution). $H_2O_2$ (30% w/w; Sigma-Aldrich, MO) was diluted in HBSS/BSA wash solution (250 µM) and was applied immediately to designated wells. Following a 1 hour incubation, cells were washed with HBSS/BSA wash solution. Cells were then incubated in EGM-2 media for an additional 72 hours. Supernatants were then collected and cells were counted for further experimental analysis.

Enzyme Linked Immunosuppressant Assay

To measure rapamycin's effect on HUVEC inflammatory cytokine levels, human interleukin-6 and interleukin-8 enzyme linked immunosuppressant assays were purchased from BD (Fischer Scientific, MA). Assays were performed on 72 hours supernatant collected from in vitro rapamycin experiments following manufacture protocol (BD Biosciences, CA).

Western Blot Analysis

HUVEC were treated with a pro-inflammatory cocktail of EGM-2 medium plus various cytokines (10 ng/mL IL-1β, 50 ng/mL INF-γ, 50 ng/mL TNF-α), as well as 10 or 100 ng/mL concentrations of free rapamycin, RaM, or TRaM. Cells were then lysed using mammalian protein extraction reagent (Pierce, IL) supplemented with Halt Protease and Phosphatase Inhibitor Cocktails. Lysates were centrifuged at 10,000 rpm for 15 minutes. All western blot reagents were purchased from Bio-Rad (CA) unless specified. The protein concentration of each lysate was determined via Bradford calorimetric Assay (Thermo Scientific, PA; 232225), and 1.6 µg of protein from each whole cell lysate was added to a 4-20% precast gel and subjected to SDS-page electrophoresis. Protein was transferred to a PVDF membrane by semi-dry transfer, where it was stained with anti-MHC class I antibody (W6) and blocked overnight with TBS-T (Tris-Buffered Saline-Tween 20) containing 5% nonfat dry milk and 0.5% BSA. An appropriate HRP-conjugated secondary antibody was added to fresh block solution at a 1:1000 dilution to incubate for 1 hour at room temperature. The protein band was then detected by enhanced chemiluminescence (ECL).

Confocal Microscopy

For visualization studies of cellular internalization of NPs, HUVEC were plated on 35 mm glass dishes (MatTek Corp., MA) and grown to confluence. NP solutions were prepared as described previously. Growth medium was replaced by NP solutions (10 or 100 ng/mL) or EGM-2 vehicle. Cells were incubated for either 6 or 24 hours. After incubation, cells were washed with EGM-2 and fixed with (4% w/w) paraformaldehyde (Affymetrix, CA) at room temperature for 5 minutes. Cellular internalization of the Dylight 680-conjugated NPs was visualized using an Olympus Fluoview FV10i LIV Confocal Microscope (Olympus, NC), 60× objective. Mean fluorescence intensity calculated and analyzed by ImageJ (NIH). All fluorescence intensities were normalized to vehicle control images.

Statistical Analysis

All data is expressed as mean±SD. All data analysis was performed using GraphPad Prism software version 6 (CA) unless specified. Multiple variables were analyzed via analysis of variance techniques, p value<0.05 was considered statistically significant.

Results

Figure 2A:
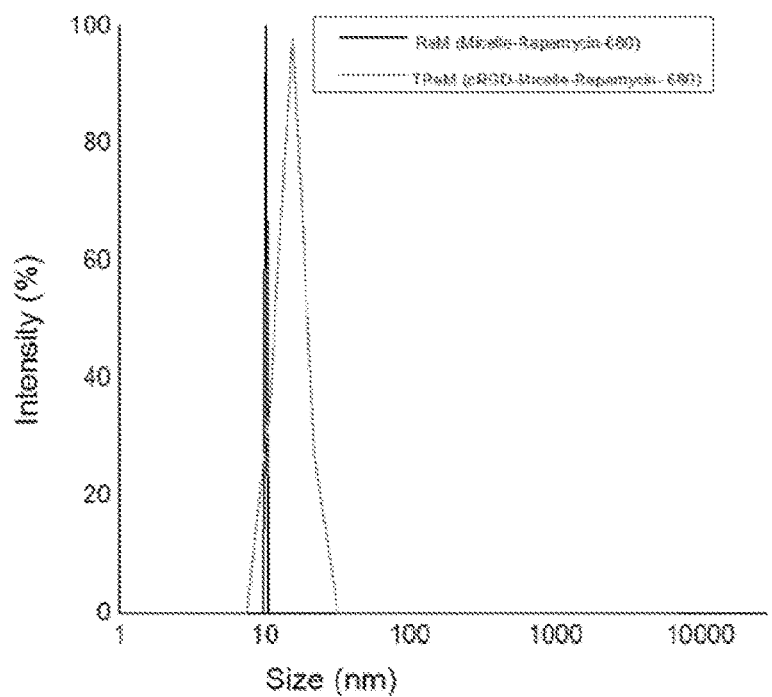
FIGS. 2A and 2B show characterization of TRaM size and Rapamycin loading.
Figure 2B:
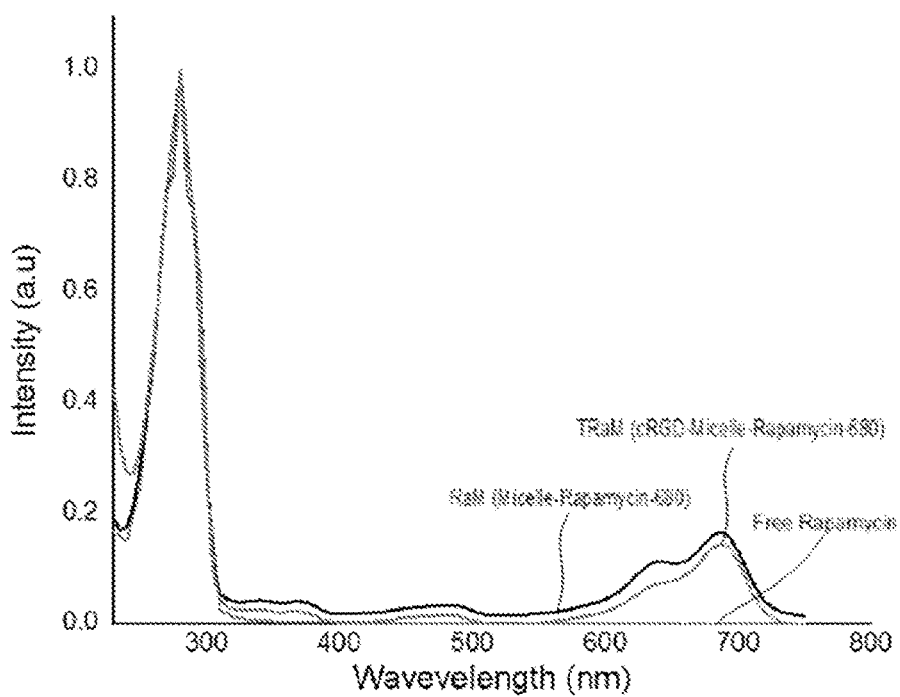

Two nanocarrier constructs were synthesized for in vitro analysis: Rapamycin Micelles (RaM) and Arginine-Glycine-Aspartate (cRGD) Targeted Rapamycin Micelles (TRaM). These rapamycin-containing micelles were synthesized using PEG-PE-amine and N-palmitoyl homocysteine (PHC) (FIG. 1) Amine functionality on PEG-PE amine was utilized for further tailoring of the micelle with the targeting cyclic peptide arginine-glycine-aspartate (cRGD) moiety, and labeled with the fluorescent dye, Dylight 680, for tracking the micelle in in vitro cellular uptake studies. Results reveal that RaM are relatively monodisperse and measure at 10 nm in size (FIG. 2A). Conjugation of TRaM with cRGD peptide shifts the size of the nanocarriers to approximately 12 nm in size. Using dynamic light scattering (DLS), size distribution was found to be identical to the instrumental response function corresponding to a monodispersed sample, indicating that aggregation is negligible. It is noteworthy that the hydrodynamic value is expected to be larger than the actual diameter because of the counter-ion cloud contributions to particle mobility (Cecka, J. M. Clinical transplants 1-20 (2002)). UV-Vis spectra (FIG. 2B) of RaM and TRaM shows the rapamycin and Dylight 680 excitation at 270 nm and 680 nm, respectively, demonstrating encapsulation and conjugation, respectively, of both components. The concentration of the encapsulated rapamycin is calculated using UV-Vis spectroscopy; each batch is purified and concentrated for consistency.

Figure 3:
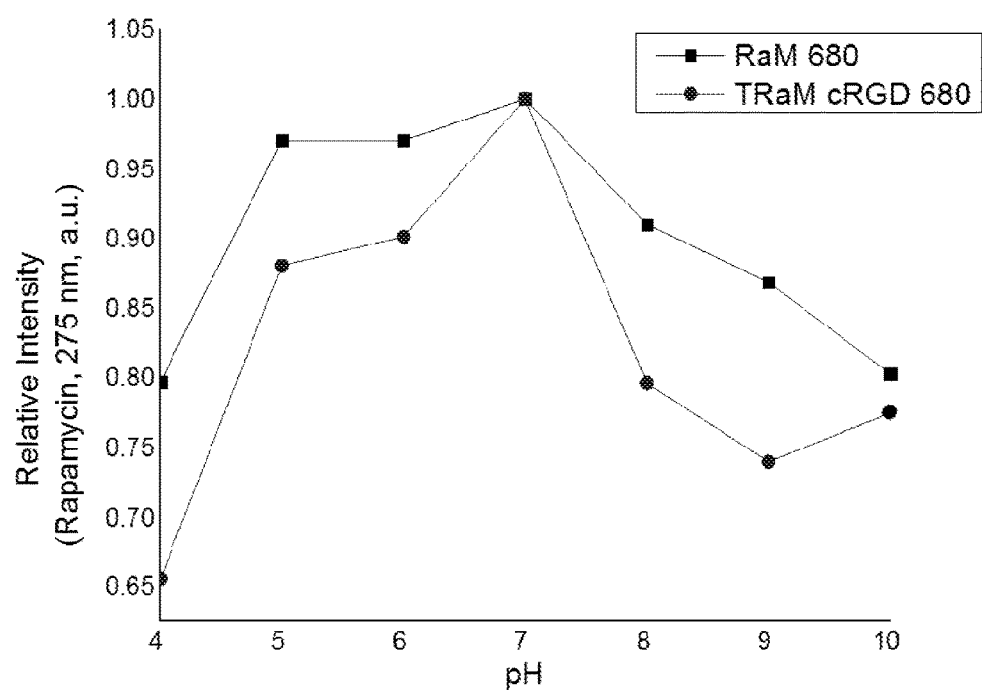
FIG. 3 shows disruption of TRaM at varying pH. An increase in fluorescence intensity of rapamycin (275 nm) filled nanoparticles between pH 7 and 8 is lost outside of the physiologic range due to NP rupture.

PHC is a pH sensitive lipid (Connor, J. & Huang, L. The Journal of cell biology 101:582-589 (1985); Collins, D., et al. Biochimica et biophysica acta 987:47-55 (1989)), which disrupts at an approximate pH of 5.0. An increase in fluorescence intensity was seen between a pH of 7.0 and 8.0 indicating that the micelle remains intact for both RaM and TRaM in this range. These results suggest that the NPs hold the hydrophobic rapamycin inside its core and resist rupture at physiologic pH. However, at a pH lower than 7 and higher than 8, the fluorescence intensity significantly decreases indicating the rupture of the micelle due to the pH sensitive lipid composition. Rapamycin is released from the micelle and quickly aggregates within the hydrophilic solvent. Upon rupture, NPs are then removed from the optical path of the excitation wavelength (FIG. 3). The drugs are encapsulated inside the hydrophobic micellar core, which reduces the interaction of the drug with the cellular environment prior to micelle disruption. Encapsulation can potentially decrease cytotoxicity of the drug and subsequent side effects of parenchymal absorption.

Figure 4A:
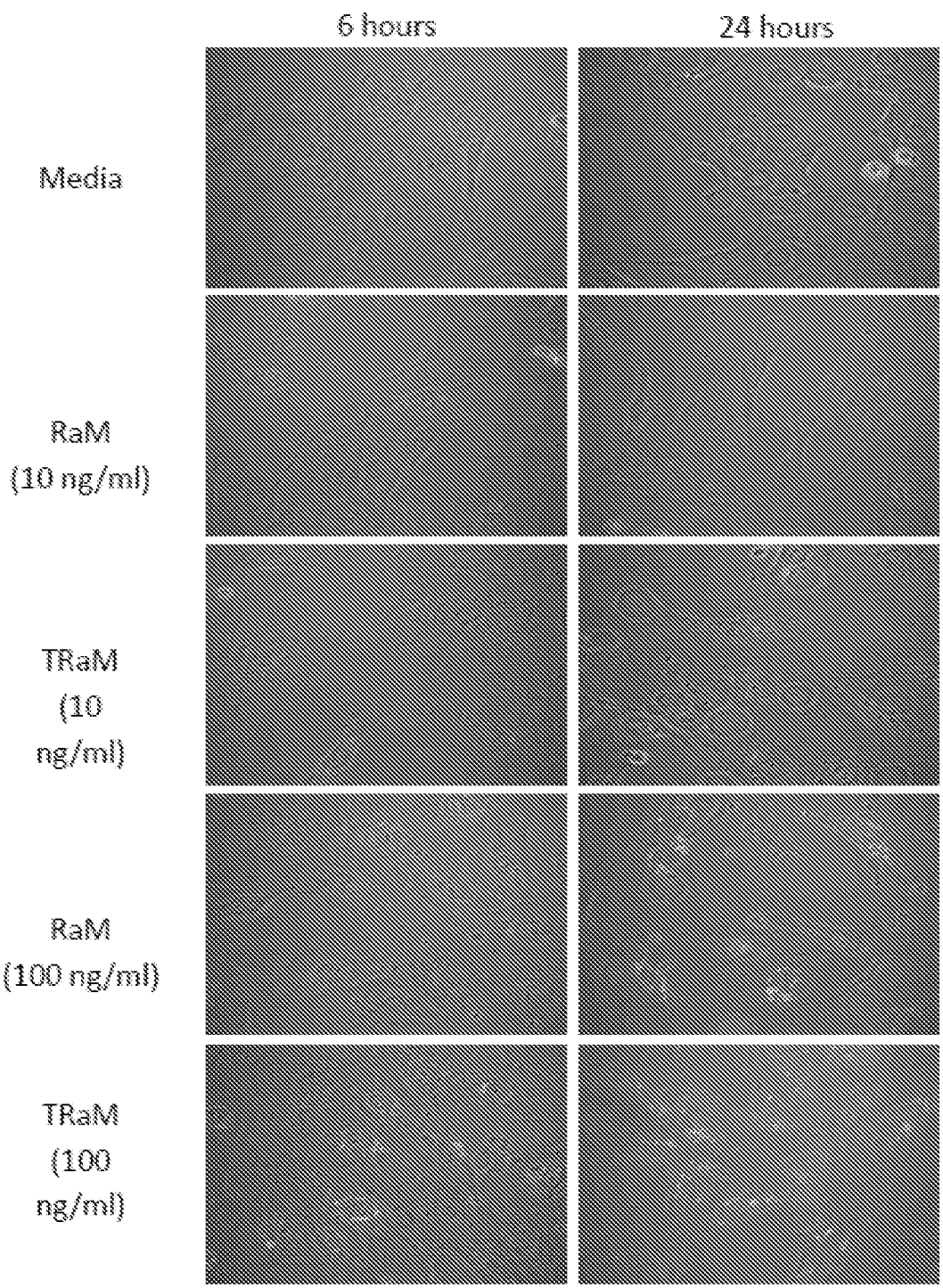
FIGS. 4A to 4C show internalization and accumulation of TRaM into HUVEC.
Figure 4B:
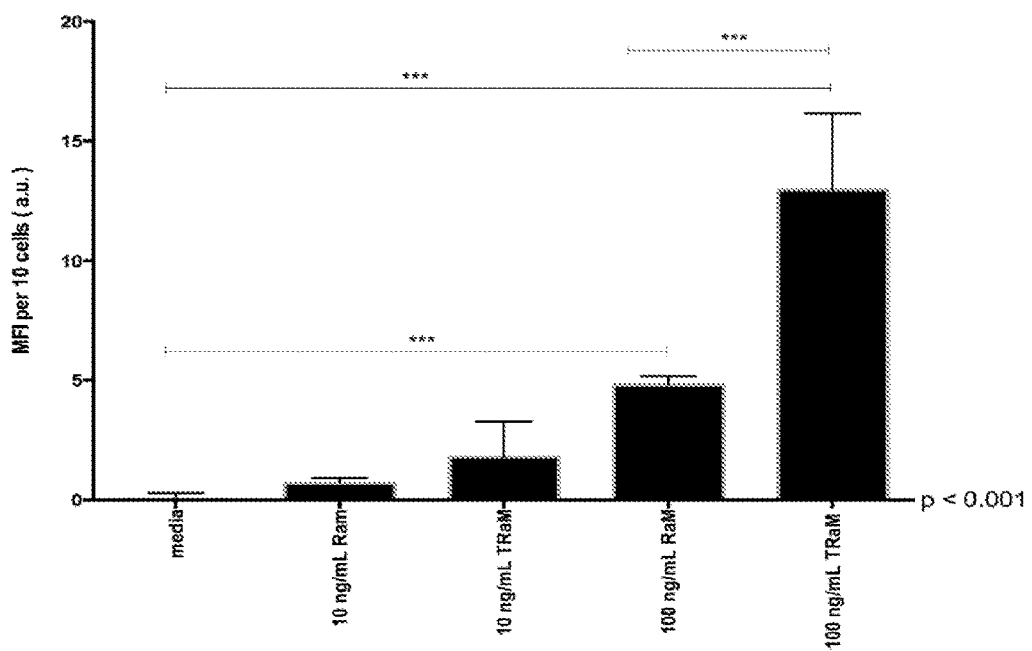
Figure 4C:
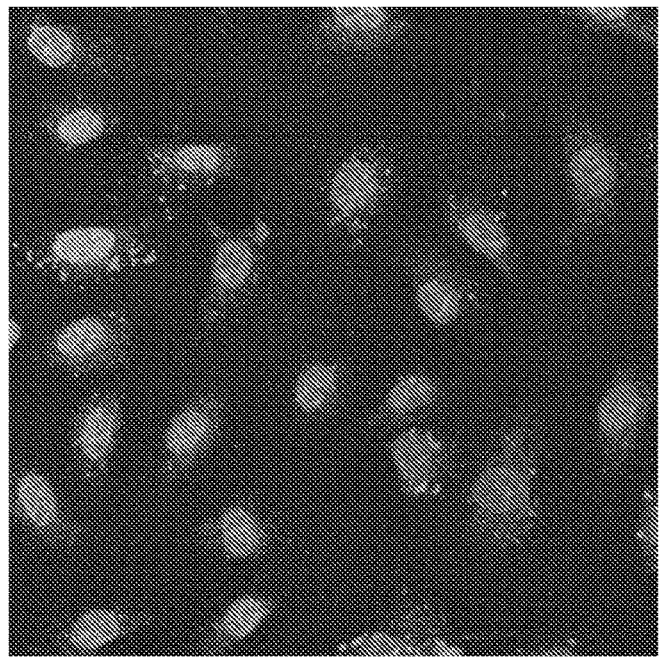

For targeting purposes, micelles were decorated with cRGD to target the αVβ3 integrin on EC surfaces to facilitate cellular uptake (FIG. 4A). To examine the intracellular uptake of our RaM and TRaM, human EC were incubated with these constructs for 6 and 24 hours periods and subsequently examined for micelle accumulation by visualization of the Dylight 680 fluorophore on the micelles surface by confocal microscopy. Internalization was observed as early as 6 hours after incubation and internalization was concentration dependent (FIG. 4B). Targeting with cRGD significantly improved the micelle internalization by more than 50% as compared to untargeted RaM. αVβ3 integrin is well-characterized for its function related to angiogenesis as well as its expression on human EC. Additionally, cRGD has also been established as a prime candidate for targeting cells expressing αVβ326. The HUVEC cells used within these experiments were confirmed to express αVβ3 and contain TRaM (FIG. 4c).

Figure 5A:
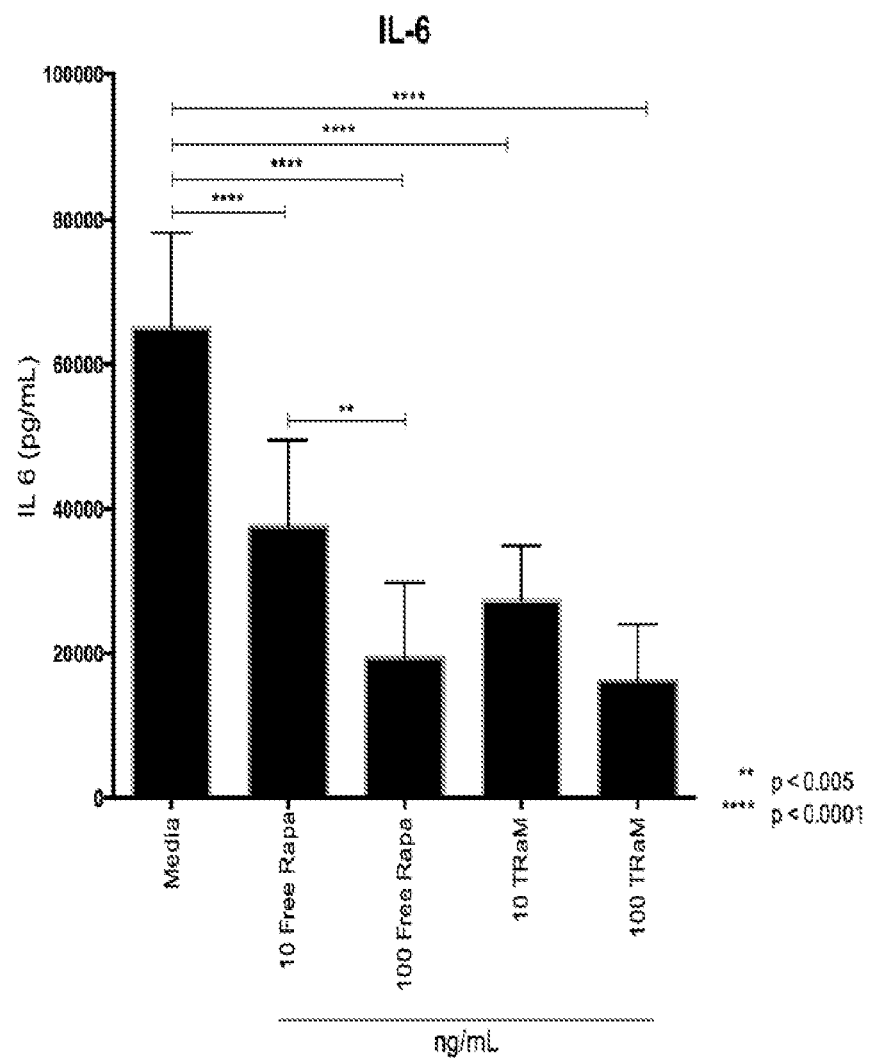
FIGS. 5A and 5B show suppression of EC inflammation by TRaM internalization and release. ELISA were performed to assess the ability of TRaM to suppress biomarkers of EC inflammation. IL-6 (FIG. 5A) and IL-8 (FIG. 5B) were analyzed as markers of EC activation. HUVEC were subjected to oxidative stress with $H_2O_2$ and treated with either free rapamycin or TRaM (10 ng/ml or 100 ng/ml). IL-6 (FIG. 5A) and IL-8 (FIG. 5B) were significantly suppressed by TRaM nanotherapy when compared to media alone, showing biological efficacy of targeted immunosuppressant nanotherapy in vitro, and had a similar effect as free rapamycin (IL-6; **$p<0.0001$; $p<0.005$; IL-8: *$p<0.05$; $p<0.005$).
Figure 5B:
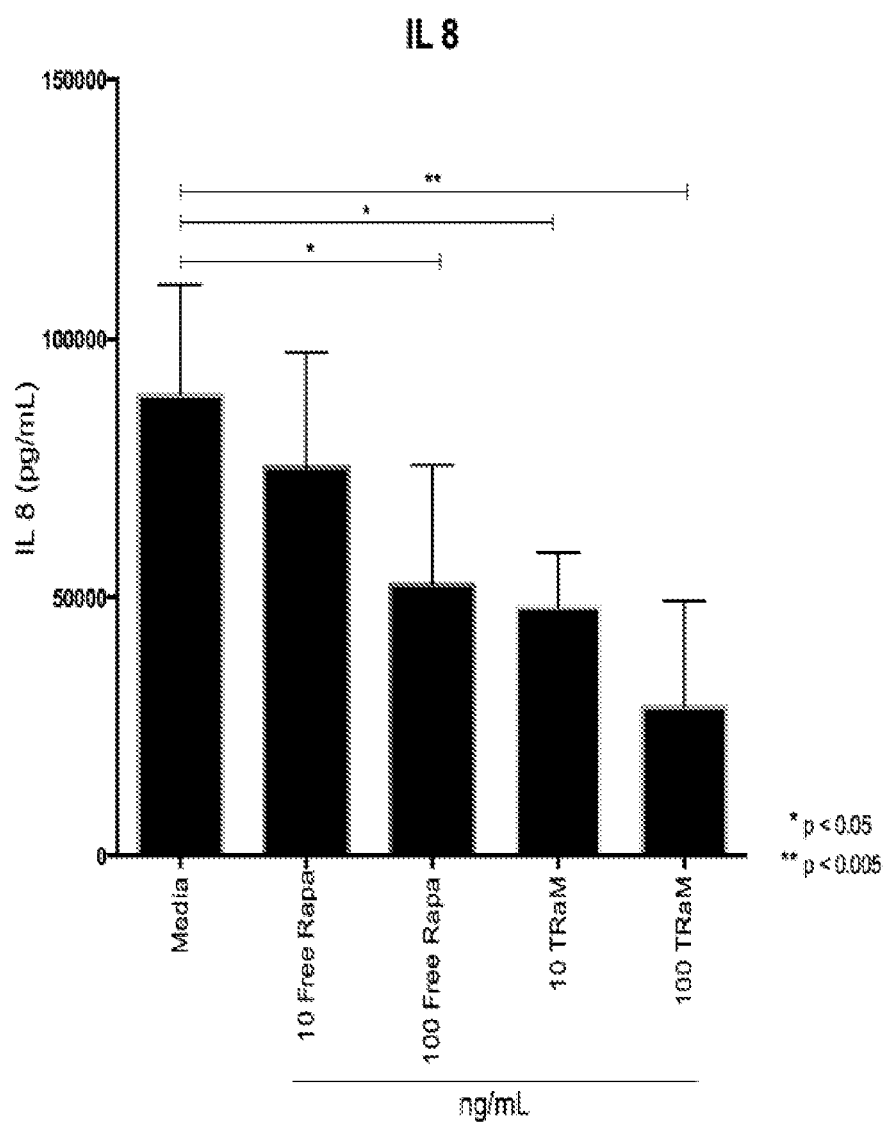

Given these data, the biologic efficacy of these targeted micelles was assessed. To determine the potential impact of local targeted delivery of rapamycin for later translation to organ transplantation, in vitro culture experiments were performed using a cell system to model the impact of reperfusion injury on EC activation and antigen presentation capacity. The endothelium is the first site of donor organ interface with the recipient and is particularly susceptible to ischemia reperfusion injury. Further, the endothelium plays an important role in priming of the adaptive immune system, which contributes to the tempo and severity of the recipient rejection response. Human primary HUVEC that mimic the in vivo vascular target were treated with $H_2O_2$ in order to mimic the oxidative stress that occurs during the ischemia/reperfusion phase of solid organ transplantation. Cells were treated with 10 ng/ml and 100 ng/ml of both free rapamycin as well as TRaM constructs (Kwon, Y. S., et al. Investigative ophthalmology & visual science 46:454-460 (2005)). Oxidative injury to endothelial cells induces endothelial activation, which results in a pro-inflammatory phenotype that is characterized by the production and release of the pro-inflammatory cytokines, IL-6 and IL-8. $H_2O_2$ exposure significantly increased EC production of IL-6 and IL-8, and TRaM therapy significantly blunted this response. Taken together, these data suggest that targeted drug delivery demonstrates equivalent efficacy to standard therapy in the face of oxidative stress injury (FIG. 5).

Figure 6:
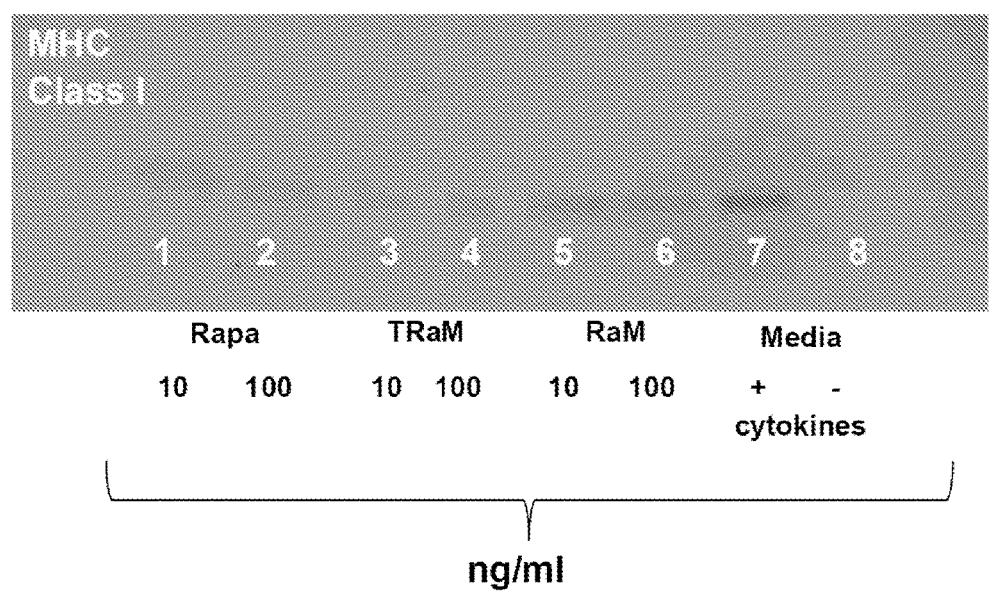
FIG. 6 shows TRaM therapy suppresses endothelial MHC expression. MHC I expression was determined in HUVEC cell lysates. Under normal conditions, HUVEC express low levels of MHC I (Lane 8). Upon stimulation with proinflammatory cytokines (IL-1β, INFγ, and TNFα) that mimic inflammatory conditions and endothelial activation, MHC I expression is significantly increased (Lane 7). HUVEC cultured with TRaM showed a marked decrease in the level of MHC I expression (Lanes 3 & 4) when compared to baseline controls (Lane 8). Additionally, TRaM therapy more efficiently suppressed MHC I levels when compared to that of untargeted RaM cultured HUVEC (Lanes 5 & 6). TRaM therapy was as effective as conventional free rapamycin therapy in its ability to suppress molecules necessary for T cell antigen presentation (Lanes 1 & 2).
Figure 7:
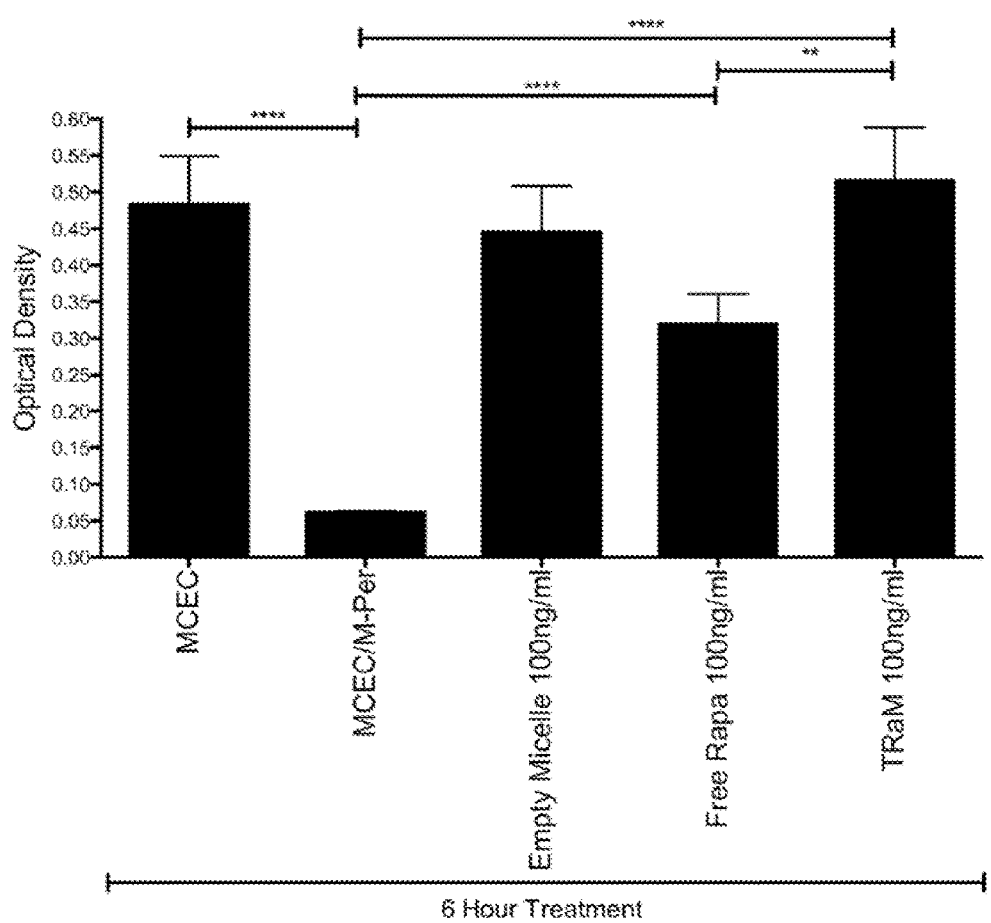
FIG. 7 shows cell viability of mouse cardiac endothelial cells (MCEC) after 6 hours of treatment with TRaM therapy compared to empty micelles or free rapamycin. Neither the micelles nor rapamycin filled micelles are toxic to the endothelial cells as viability is maintained.
Figure 8A:
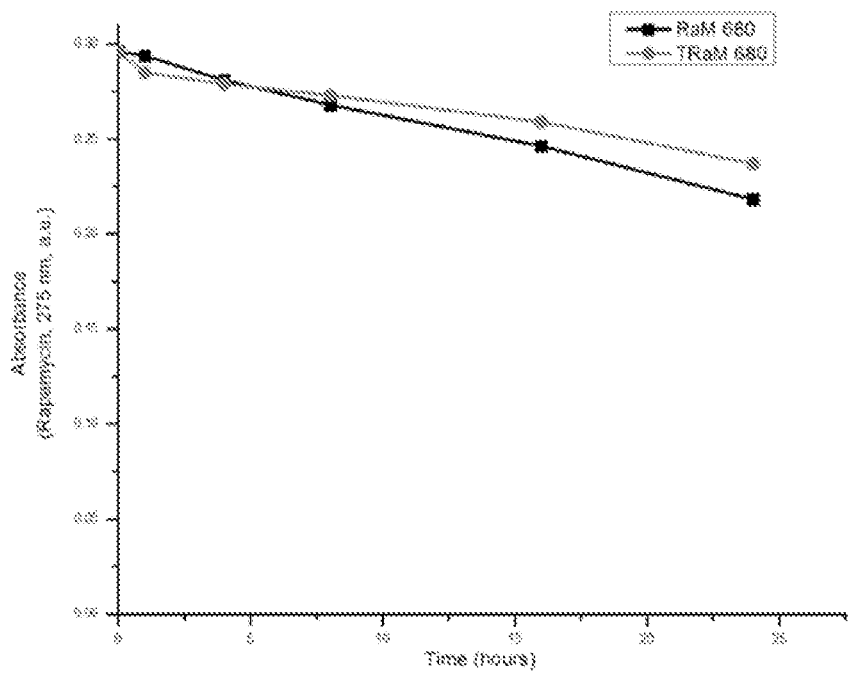
FIGS. 8A and 8B are graphs showing stability of RaM 680 (■) and TRaM 680 (●) micelles (absorbance) as a function of time in saline (FIG. 8A) vs. 10% fetal bovine serum (FBS) (FIG. 8B). TRaM and untargeted RaM remain stable and intact as evidenced by the retention of their fluorophore integrity over time. The nanoparticles are able to maintain their stability in both saline and serum media.
Figure 8B:
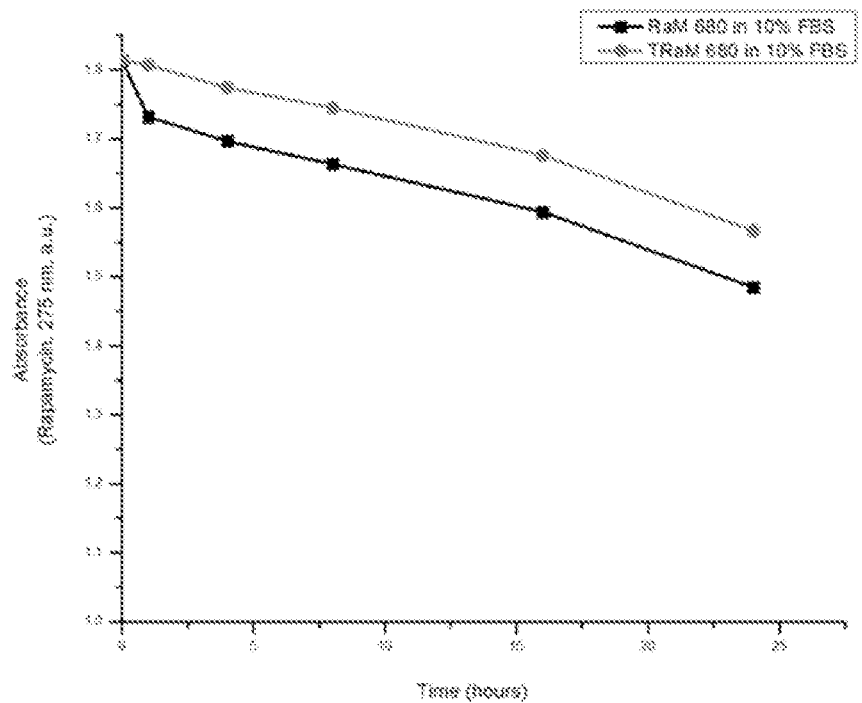
Figure 9:
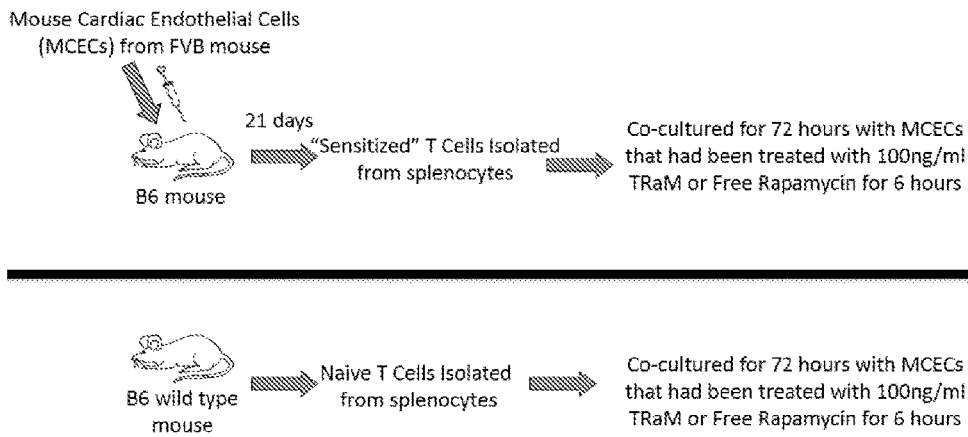
FIG. 9 illustrates an experiment designed to evaluate the impact of TRaM on T cell function. MCECs from an FVB mouse are injected into a B6 mouse. After 21 days, "sensitized" T cells are isolated from splenocytes. These sensitized T-cells and Naïve T cells isolated from splenocytes of B6 wildtype mice are each co-cultured for 72 hours with MCECs that have been treated for 6 hours with 100 ng/ml TRaM or free rapamycin. TRaM therapy significantly diminished the secretion of IFN-γ by "memory" T cells when stimulated by endothelial cells in comparison to untreated cultures.
Figure 10A:
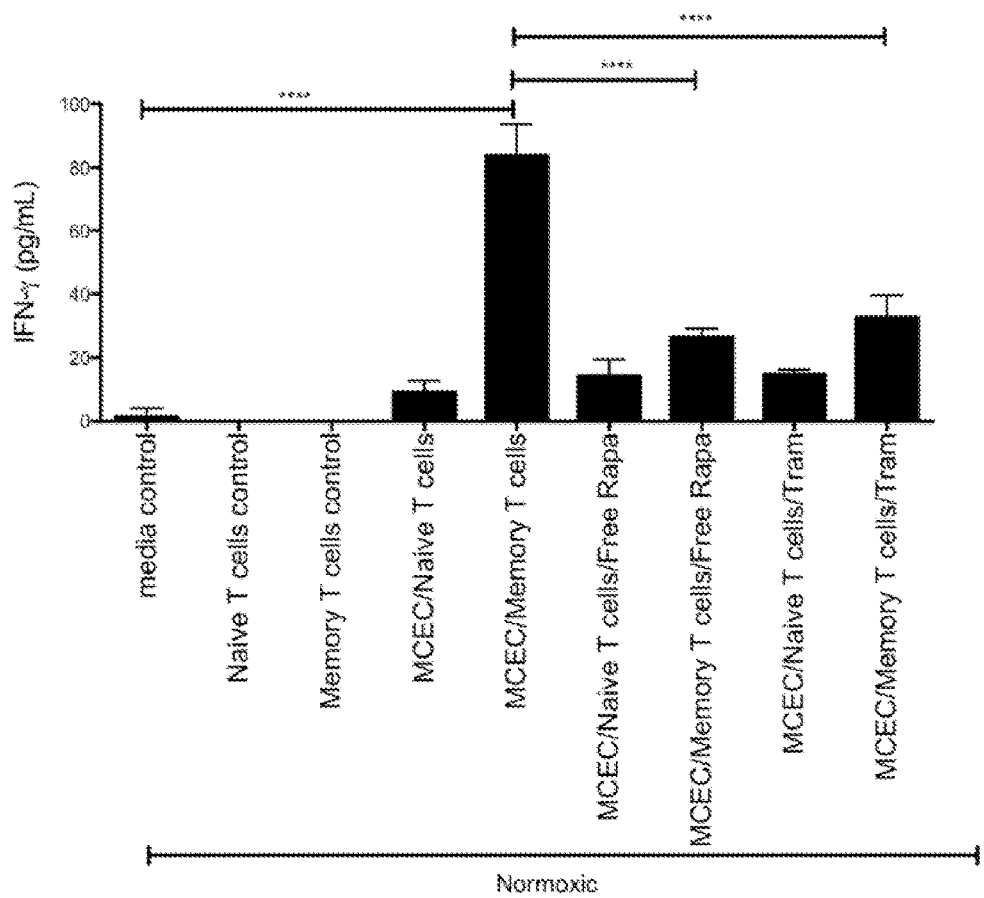
FIGS. 10A and 10B show normoxic (FIG. 9A) and hypoxic (FIG. 9B) IFN-γ (pg/ml) expression by the cells from FIG. 8. TRaM therapy maintains its ability to dampen IFN-γ production by "memory" T cells in stressful environments of normal and low oxygen tension.
Figure 10B:
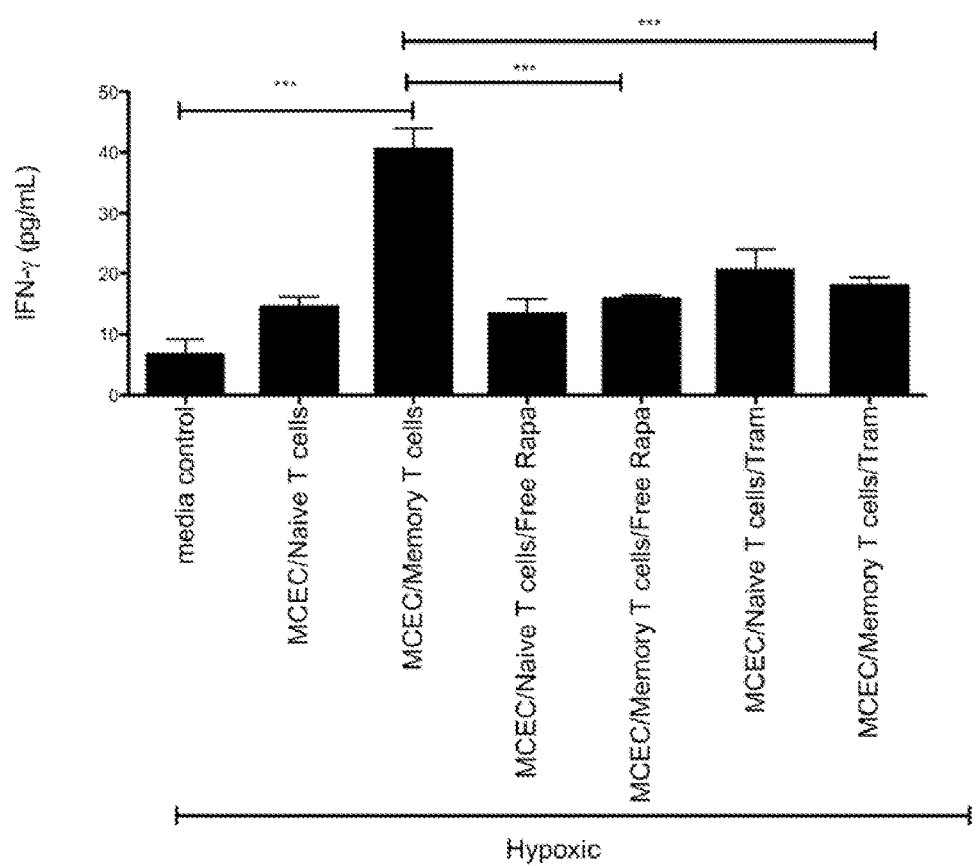
Figure 11:
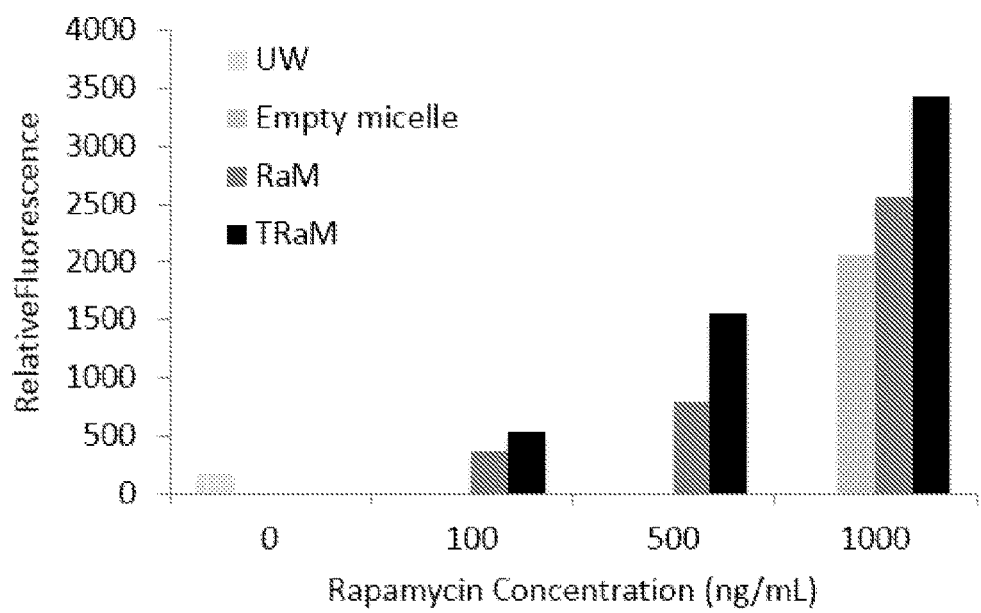
FIG. 11 is a bar graph showing relative ex vivo fluorescence of trachea soaked with University of Wisconsin (UW) solution, empty micelle, RaM, or TRaM containing 0, 100, 500 or 1000 ng/ml rapamycin. TRaM and RaM are taken up in a dose dependent manner by tracheal tissue procured and soaked in TRaM or RaM enhanced preservation solution (University of Wisconsin Solution). Targeting clearly allows for improved absorption of nanotherapy as evidenced by brighter intensity.
Figures 12A, 12B, 12C, 12D:
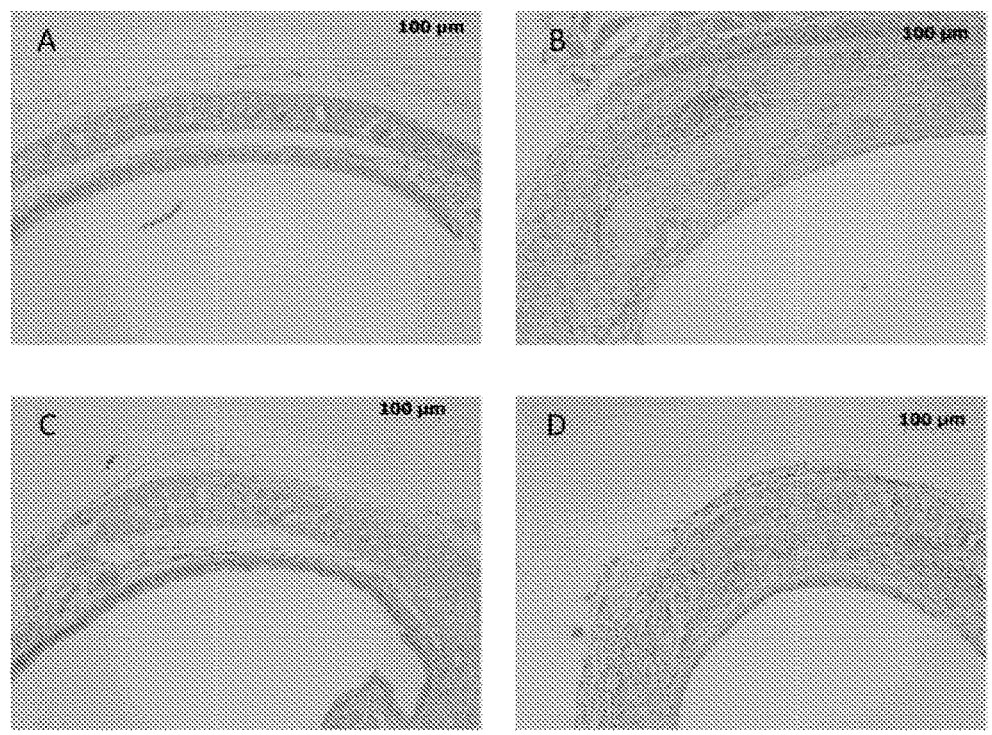
FIGS. 12A to 12D show Balb/c control donor tracheas (FIG. 12A) or donor tracheas after being stored in UW solution containing either free rapamycin (FIG. 12D), TRaMs (FIG. 12C), or no additives (FIG. 12B) for 4 hrs at 4° C. prior to orthotopic transplantation into allogeneic C57Bl/6 recipient. Twenty eight days later transplanted tracheas were harvested and assessed for the degree of chronic rejection. Note the increased fibrosis, inflammation and presence of squamous epithelium in UW stored tracheas. Treatment with TRaMs or Free Rapamycin reduced fibrosis, inflammation and preserved normal pseudo stratified respiratory epithelium as compared to UW alone, with the degree of protection significantly improved in TRaM treated grafts.

At the time of organ implantation, donor EC are capable of presenting the foreign antigen of donor organs in the context of their major histocompatibility complexes (MHC) to host lymphocytes. This allopresentation is an instrumental event in initiating rejection and the expansion of destructive alloreactive memory T cells. The insult of IRI is well-known to up regulate the endothelial expression of MHC. Clinically, therapies that can reduce this exaggerated expression of MHC and foreign antigen are likely to minimize organ rejection and improve graft outcomes. To test this hypothesis, EC were treated with a potent inflammatory cytokine cocktail present during IRI (10 ng/mL IL-1β, 50 ng/mL INF-γ, 50 ng/mL TNF-α) and known to induce endothelial activation. Human EC robustly express MHC molecules, such as MHC I, when subjected to this pro-inflammatory environment. Additionally, cells treated with varying doses of free rapamycin are able to down regulate these molecules, and thus the antigen presentation capacity and immunogenicity of the HUVECs. Interestingly, TRaM therapy was also able to suppress the expression of MHC I similar to standard rapamycin therapy and more efficiently than untargeted RaM therapy (FIG. 6.) Taken together, these data suggest that TRaM therapy can not only reduce pro-inflammatory cytokine production and innate immune mechanisms, but also impact adaptive immunity post transplantation by modulating EC expression of MHC molecules.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A targeted nanocarrier, comprising an effective amount of an immunosuppressive agent encapsulated in a micelle that comprises on its surface a peptide or peptidomimetic that binds Complement component 3 (C3) breakdown products and reperfusion epitopes, a peptide or peptidomimetic that binds an integrin, or a combination thereof, wherein the peptide or peptidomimetic that binds C3 breakdown products comprises a Complement Receptor type 2 (Cr2) peptide or peptidomimetic;

wherein the peptide or peptidomimetic that binds an integrin comprises the amino acid sequence Arg-Gly-Asp (RGD); and wherein the nanocarrier has a mean diameter of 10 nm to 15 nm.

2. The targeted nanocarrier of claim 1, wherein the micelle is pH sensitive, temperature sensitive, or a combination thereof.

3. The targeted nanocarrier of claim 2, wherein the micelle comprises N-palmitoyl homocysteine (PHC).

4. The targeted nanocarrier of claim 1, wherein the micelle comprises amino-polyethylene glycol-phosphatidylethanolamine (PEG-PE-Amine).

5. The targeted nanocarrier of claim 1, wherein the peptide or peptidomimetic that binds an integrin comprises a cyclized RGD (cRGD) peptide or peptidomimetic.

6. The targeted nanocarrier of claim 1, wherein the immunosuppressive agent comprises a mammalian target of rapamycin (mTOR) inhibitor, a calcineurin inhibitor, or a combination thereof.

7. The targeted nanocarrier of claim 1, wherein the immunosuppressive agent comprises rapamycin or a derivative thereof.

8. The targeted nanocarrier of claim 1, wherein the immunosuppressive agent comprises tacrolimus or a derivative thereof.

9. The targeted nanocarrier of claim 1, wherein the immunosuppressive agent comprises cyclosporin A or a derivative thereof.

10. The targeted nanocarrier of claim 1, wherein the immunosuppressive agent comprises a nuclear factor kappa-light-chain-enhancer of activated B cells (NFkB) inhibitor.

11. The targeted nanocarrier of claim 1, wherein the immunosuppressive agent comprises a Janus kinase 3 (JAK3) inhibitor.

12. The targeted nanocarrier of claim 1, wherein the immunosuppressive agent comprises Interleukin 2 (IL-2) R alpha.

13. The targeted nanocarrier of claim 1, wherein the immunosuppressive agent comprises Complement C siRNA.

14. The targeted nanocarrier of claim 1, wherein the immunosuppressive agent comprises B-cell proteasome inhibitors.

15. The targeted nanocarrier of claim 1, wherein the immunosuppressive agent comprises mycophenolate or a derivative thereof.

* * * * *